United States Patent

Zipplies et al.

[11] Patent Number: 5,126,374
[45] Date of Patent: Jun. 30, 1992

[54] FUNGICIDAL GUANIDINES

[75] Inventors: Matthias Zipplies, Hirschberg; Hubert Sauter, Mannheim; Franz Roehl; Eberhard Ammermann, both of Ludwigshafen; Gisela Lorenz, Neustadt, all of Fed. Rep. of Germany

[73] Assignee: BASF Aktiengesellschaft, Ludwigshafen, Fed. Rep. of Germany

[21] Appl. No.: 547,194

[22] Filed: Jul. 3, 1990

[30] Foreign Application Priority Data

Jul. 6, 1989 [DE] Fed. Rep. of Germany ....... 3922232

[51] Int. Cl.$^5$ ................. A61K 31/155; C07C 279/16; C07C 279/08; C07C 295/00
[52] U.S. Cl. ................................ 514/634; 514/238.5; 514/331; 514/427; 544/162; 544/163; 544/165; 544/170; 544/177; 546/194; 546/246; 548/561; 558/303; 558/391; 558/419; 558/422; 558/426; 558/430; 558/431; 558/432; 564/230; 564/237
[58] Field of Search ............... 564/230, 237; 514/634

[56] References Cited

U.S. PATENT DOCUMENTS

| | | | |
|---|---|---|---|
| 3,109,859 | 11/1963 | McKay et al. | 260/564 |
| 3,320,229 | 5/1967 | Szabo et al. | 260/96.5 |
| 3,961,056 | 6/1976 | Du Charme | 424/248 |
| 4,427,685 | 1/1984 | Stemp | 424/267 |

FOREIGN PATENT DOCUMENTS

| | | |
|---|---|---|
| 0358018 | 3/1990 | European Pat. Off. . |
| 2133056 | 1/1973 | Fed. Rep. of Germany . |
| 3108564 | 11/1982 | Fed. Rep. of Germany . |
| 0925455 | 5/1963 | United Kingdom . |
| 1026402 | 4/1966 | United Kingdom . |
| 1111563 | 5/1968 | United Kingdom . |

OTHER PUBLICATIONS

Chemie der Pflanzenschutz-und Schadlingsbedampfungsmittel, 4 145–148 (1977).
J. Org. Chem. 51, 1882–1884 (1986).
J. Medicinal Chem., 12, 712–715 (1963).

Primary Examiner—Glennon H. Hollrah
Assistant Examiner—P. O'Sullivan
Attorney, Agent, or Firm—Keil & Weinkauf

[57] ABSTRACT

Guanidines I

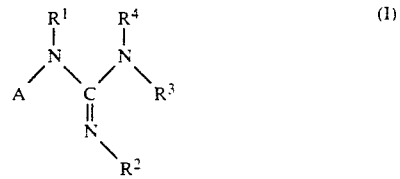

($A = C_5-C_{12}$-cycloalkyl which may bear up to three further substituents; benzyl substituted in the para-position; $R^1$, $R^2$, $R^3 = H$, $C_1-C_4$-alkyl; $R^4 = C_5-C_{18}$-alkyl which may be interrupted by oxygen, $C_5-C_{18}$-alkenyl, $C_4-C_{18}$-alkynyl or phenyl-$C_1-C_6$-alkyl, and these groups may bear up to three further substituents and the phenyl moiety of the phenylalkyl may additionally bear a phenoxy group or up to three $C_2-C_4$-alkenyl, $C_1-C_4$-alkoxy-$C_1-C_4$-alkyl, $C_1-C_6$-alkyl or haloalkyl groups, $C_5-C_6$-cycloalkyl-$C_1-C_8$-alkyl, where the ring may bear up to three further substituents; A=benzyl and $R^4 = C_3-C_4$-alkyl which may be interrupted by oxygen, or $C_4$-alkenyl, both of which may bear up to three further substituents; $R^3 + R^4 = C_5-C_6$-heterocycle which may bear up to three further substituents and may be interrupted by oxygen) and the salts I.HX and the metal complexes of I.

The compounds I are suitable as fungicides.

6 Claims, No Drawings

FUNGICIDAL GUANIDINES

The present invention relates to novel guanidines of the formula I

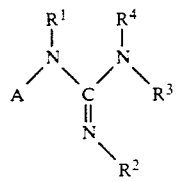

where

A is cycloalkyl which has 5 to 12 carbon atoms in the ring and may carry up to three of the following substituents: hydroxyl, halogen, $C_1$–$C_{10}$-alkyl, $C_1$–$C_{10}$-alkoxy, $C_1$–$C_{10}$-haloalkyl and $C_1$–$C_8$-alkoxy-$C_1$–$C_8$-alkyl; or benzyl which is substituted in the para position by $C_1$–$C_{10}$-alkyl or $C_1$–$C_{10}$-alkoxy, where the substituent may furthermore carry a hydroxyl or a $C_1$–$C_6$-alkoxy group;

$R^1$, $R^2$ and $R^3$ are each hydrogen or $C_1$–$C_4$-alkyl, and $R^4$ is $C_5$–$C_{18}$-alkyl which may be interrupted by oxygen, or is a $C_5$–$C_{18}$-alkenyl group, a $C_1$–$C_{18}$-alkynyl group or a phenyl-$C_1$–$C_6$-alkyl group, where these groups may carry up to three of the following substituents: hydroxyl, halogen, cyano, $C_1$–$C_7$-alkoxy or up to two amino, $C_1$–$C_4$-alkylamino or di-($C_1$–$C_4$)-alkylamino substituents and the phenyl moiety of the phenylalkyl group may additionally carry a phenoxy group or up to three $C_2$–$C_4$-alkenyl groups, $C_1$–$C_4$-alkoxy-$C_1$–$C_4$-alkyl groups or $C_1$–$C_6$-alkyl groups which may be unsubstituted or partially or completely halogenated, or $C_5$- or $C_6$-cycloalkyl-$C_1$–$C_8$-alkyl where the cycloalkyl ring may carry up to three $C_1$–$C_4$-alkyl groups or up to two hydroxyl or trifluoromethyl groups; or, where A is a benzyl group according to the definition, $C_3$- or $C_4$-alkyl which may be interrupted by oxygen or may carry a $C_4$-alkenyl group, where these groups may carry up to three of the following substituents: hydroxyl, halogen, cyano, $C_1$–$C_7$-alkoxy or up to two amino, $C_1$–$C_4$-alkylamino or $C_2$–$C_8$-dialkylamino groups; or, together with the radical $R^3$ and the nitrogen atom, may form a 5-membered or 6-membered heterocyclic ring which may be monosubstituted to trisubstituted by $C_1$–$C_6$-alkyl, phenyl or $C_1$–$C_6$-alkylphenyl or may be interrupted by an oxygen atom, and the plant-tolerated mineral acid salts I·HX and metal complexes of I.

The present invention frthermore relates to processes for the preparation of these compounds, their use as fungicides, and fungicides which contain these compounds as active substances.

The monograph Chemie der Pflanzenschutz- und Schädlingsbekämpfungsmittel, Volume 4, Springer Verlag 1977, page 145 et seq., discloses fungicidal alkylguanidine salts (dodines) and bisalkylguanidineamine salts (guazatines) which carry an alkyl group on one of the guanidine nitrogen atoms or whose guanidino groups are linked to one another by an azaalkylene group.

Guanidine derivatives which have a fungicidal action and are aryl-substituted at one nitrogen atom and substituted by alkyl and cycloalkyl groups at the two other nitrogen atoms are described in DE-A1-31 08 564.

However, the actions of these compounds may be satisfactory only under certain circumstances, particularly in the case of low application rates and concentrations. In particular, some of them cause damage to crops.

It is an object of the present invention to provide novel fungicidal compounds which, even at relatively low application rates, have better fungicidal properties than the compounds known to date, without causing significant damage to the crops.

We have found that this object is achieved by the guanidines of the formula I which were defined at the outset. We have also found processes for the preparation of these guanidines.

If $R^1$ and/or $R^3$ are hydrogen, the compounds I may furthermore be present in tautomeric forms, which are described by formula I.

The substituents in the novel compounds I have the following specific meanings:

A is cyclopentyl, cyclohexyl, cycloheptyl, cyclooctyl or cyclododecyl, where these groups may carry up to three of the following radicals:

hydroxyl;

halogen, including in particular fluorine;

straight-chain or branched $C_1$–$C_{10}$-alkyl, in particular $C_1$–$C_6$-alkyl, such as methyl, ethyl, propyl, isopropyl, butyl, isobutyl, sec-butyl, tert-butyl, 1,1-dimethylpropyl or 2,4,4-trimethylpent-2-yl; straight-chain or branched $C_1$–$C_{10}$-alkoxy, in particular $C_1$–$C_6$-alkoxy, such as methoxy, ethoxy, isopropoxy, n-butoxy, tert-butoxy or octyloxy; straight-chain or branched, partially or completely halogenated $C_1$–$C_{10}$-haloalkyl, in particular haloalkyl, such as trifluoromethyl or pentafluoroethyl;

$C_1$–$C_8$-alkoxy-$C_1$–$C_8$-alkyl, in particular $C_1$–$C_4$-alkoxy-$C_1$–$C_4$-alkyl, such as methoxymethyl, ethoxymethyl, methoxyethyl, tert-butoxymethyl or 1-methoxy-1methylethyl; or benzyl which may carry one of the following substituents in the para position:

straight-chain or branched $C_1$–$C_{10}$-alkyl, in particular $C_1$–$C_6$-alkyl, such as methyl, ethyl, propyl, isopropyl, butyl, isobutyl, sec-butyl, tert-butyl, 1,1-dimethylethyl, 1,1-dimethylpropy1,2,3-dimethylpropyl, 1,1,2-trimethylpropyl, 2-hydroxyprop-2-yl or 2-methoxyprop-2-yl;

$C_1$–$C_{10}$-alkoxy, in particular $C_1$–$C_6$-alkoxy, such as methoxy, ethoxy, isopropoxy, n-butoxy, tert-butoxy or hexyloxy;

particularly preferred radicals A are cyclopentyl, cyclohexyl, cycloheptyl, 1-methoxy-1-methylethylcyclohexyl, 2-methylcyclohexyl, 3-methylcyclohexyl, 3-trifluoromethylcyclohexy, 1,3,3-dimethylcyclohexyl,3,3,5-trimethylcyclohexyl, 4-hydroxycyclohexyl, 4-chlorocyclohexyl, 4-chloroethylcyclohexyl, 4-isopropylcyclohexyl, 4-(1-methoxyisopropylcyclohexyl, 4-tert-butylcyclohexyl, 4-(1,1-dimethylpropyl)-cyclohexyl, 4-ethoxycyclohexyl, 4-tertbutoxycyclohexyl, 4-(2,4,4-trimethylhex-2-yl)-cyclohexyl, benzyl, p-methylbenzyl, p-ethylbenzyl, p-isopropylbenzyl, p-tert-butylbenzyl, p-(2,3-dimethylpropyl)-benzyl, p-(1,1-dimethylethyl)-benzyl, p-(1,1,2-trimethylpropyl)benzyl, p-(2-hydroxyprop-2-yl)-benzyl, p-(2-methoxyprop- 2-yl)-benzyl, p-methoxybenzyl or p-tert-butoxybenzyl; $R^1$, $R^2$ and $R^3$ are each preferably hydrogen, methyl, ethyl, propyl, isopropyl, n- butyl or isobutyl; $R^4$ is straight-chain or branched $C_5$–$C_{18}$-alkyl which may be interrupted by oxygen, preferably 2,2-dimethylpropyl, 3methylbutyl, 3,3-dimethylbutyl, n-pentyl, 4,4-dimethylpentyl, n-hexyl, 2-ethylhexyl, 3,5,5-trimethylhexyl, n-heptyl, n-octyl, 5-methyloct-2-yl, 2-hydroxyoctyl, 8-hydroxyoctyl, 8-fluorooctyl, 8-chlorooctyl, 2,5,7,7-tetramethyloctyl, n-nonyl, n-decyl, n-dodecyl, n-tridecyl, isotridecyl, 6,10-dimethylundec-2-yl, 6,10,14-trimethylpentadec2-yl, n-hexadecyl, n-octadecyl, 4-(4-tert-butoxy)-but-2-yl, tert-butoxypentyl, 6-ethyl-4-oxadecyl or 3-diethylaminopropyl;

straight-chain or branched $C_5$–$C_{18}$-alkenyl or $C_4$–$C_{18}$-alkyn-yl, in particular dimethylallyl or but-2-ynyl; phenyl-$C_1$–$C_6$-alkyl, in particular phenyl-$C_1$–$C_4$-alkyl, which may carry a phenoxy group or up to three of the following radicals:

hydroxyl;

halogen, including in particular fluorine or chlorine;

cyano;

straight-chain or branched $C_1$–$C_7$-alkoxy, in particular $C_1$–$C_4$-alkoxy, such as methoxy, ethoxy, isopropoxy, n-butoxy or tert-butoxy, or up to 2 amino, $C_1$–$C_4$-alkylamino and/or di-$C_1$–$C_4$-alkylamino substituents, in particular amino, dimethylamino and diethylamino;

phenoxy on the phenyl moiety of the phenylalkyl group;

up to three of the following substituents on the phenyl moiety of the phenylalkyl group:

straight-chain or branched $C_1$–$C_4$-alkoxy-$C_1$–$C_4$-alkyl, in particular $C_1$–$C_4$-alkoxy-$C_1$-or -$C_2$-alkyl, such as methoxymethyl, ethoxymethyl or ethoxyethyl;

straight-chain or branched $C_2$–$C_4$-alkenyl, in particular ethenyl or isopropenyl;

$C_1$–$C_4$-alkoxy-$C_1$–$C_4$-alkyl, such as methoxymethyl, or straight-chain or branched $C_1$–$C_6$-alkyl or partially or completely halogenated $C_1$–$C_6$-haloalkyl, in particular methyl, trichloromethyl, trifluoromethyl, ethyl, propyl, isopropyl, n-butyl, tert-butyl, 1,1-dimethylpropyl, 1,1,2-trimethylpropyl, 2,4,4-trimethylpentyl- or perfluoropentyl;

particularly preferred radicals are benzyl, 4-hydroxybenzyl, 3-chlorobenzyl, 4-chlorobenzyl, 2,4-dichlorobenzyl, 4-cyanobenzyl, 4-methylbenzyl, 4-trifluoromethylbenzyl, 4-trichloromethylbenzyl, 4-isopropylbenzyl, 4-isopropenylbenzyl, 3-tert-butylbenzyl, 4-tert-butylbenzyl, 4-(1,1-dimethylpropyl)-benzyl, 4-(1,1,2-trimethylpropyl)-benzyl, 4-(2,4,4-trimethylpentyl)-benzyl, 4-(1-hydroxy-1-methylethyl)-benzyl, 3,5-di-tert-butyl-4-hydroxybenzyl, 4-methoxybenzyl, 4-(1-methoxy-1-methylethyl)-benzyl, 4-n-butoxybenz-yl or 4-tert-butoxybenzyl, 1-phenylethyl, phenethyl, 4-methoxyphenethyl, 4-tert-butylphenethyl, 3-phenylpropyl, 3-(4-tert-butylphenyl)-2-methylpropyl or 4-phenylbut-2-yl;

a $C_5$- or $C_s$-cycloalkyl-$C_1$–$C_8$-alkyl group where the cycloalkyl ring may carry up to three $C_1$–$C_4$-alkyl groups, such as methyl or tert-butyl, or up to two hydroxyl or trifluoromethyl groups, in particular a $C_5$- or $C_6$-cycloalkyl-$C_1$–$C_4$-alkyl group, such as cyclohexylmethyl, 4-tert-butylcyclohexylmethyl, 4-trifluoromethylcyclohexylmethyl, 4-hydroxycyclohexylmethyl, 4-tert-butoxycyclohexylmethyl, cyclohexylethyl, cyclohexylpropyl or 3-(4-tert-butylcyclohexyl)-2-methylpropyl;

or, where A is a benzyl group according to the definition, straight-chain or branched $C_3$- or $C_4$-alkyl which may be interrupted by oxygen, in particular isopropyl, tert-butyl or 2-hydroxypropyl; or $C_4$-alkylene, in particular but-2-enyl;

or, together with $R^3$ and the nitrogen atom, is a 5-membered or 6-membered heterocyclic structure which may be monosubstituted to trisubstituted by $C_1$–$C_6$-alkyl, phenyl or $C_1$–$C_6$-alkylphenyl and may be interrupted by an oxygen atom; in particular 2-(1,5-dimethylhexyl)pyrrolidinyl, 2-(2,4,4-trimethylpentyl)-pyrrolidinyl, 3-phenylpyrrolidinyl, 3-(4-tert-butylphenyl)-pyrrolidinyl, 3-(4-tert-butylphenyl)-4-methylpyrrolidinyl, piperidinyl, 4-tert-butylpiperidinyl, 4-(4-tert-butylphenyl)piperidinyl, morpholinyl or 2,6-dimethylmorpholin-4-yl.

Particularly suitable compounds I are shown in the Table, those which carry the following substituents being particularly preferred:

A is cyclohexyl, 3,3-dimethylcyclohexyl, 4-tert-butylcyclohexyl or p-tert-butylbenzyl;

$R^1$ is hydrogen;

$R^2$ is hydrogen or $C_1$–$C_4$-alkyl;

$R^3$ is hydrogen or methyl; and $R^4$ is $C_6$–$C_{14}$-alkyl, in particular 2-ethylhexyl or 6,1-dimethylundec-2-yl-, or p-($C_1$–$C_6$-alkyl)-phenyl-$C_1$–$C_4$-alkyl, in particular p-tert-butylbenzyl, 3-(p-tert-butylphenyl)-2-methylpropyl or p-(2,3-dimethylbut-2-yl)-benzyl, or together with $R^3$ and the nitrogen atom, forms 4-tert-butylphenylpyrrolidinyl.

Suitable acid addition salts are the planttolerated salts of acids which do not adversely affect the fungicidal action of I, for example the iodides, chlorides, bromides, hydrochlorides, hydrobromides, sulfates, dodecylsulfates, nitrates, carbonates, phosphates, formates, acetates, propionates, benzoates, oxalates, naphthalenesulfonates, dodecylbenzenesulfonates, lactates and the salts with the anion of saccharin. The iodides, chlorides and acetates are preferred.

Suitable metal complexes are the complexes of copper, of zinc, of tin, of manganese, of iron, of cobalt or of nickel. The complexes are preferably prepared from the free bases I and salts of mineral acids, for example the chlorides or sulfates, with the metals.

The following compounds I are very particularly suitable:

N-1-cyclohexyl-N-2-(6,10-dimethylundec-2-yl)-guanidine hydriodide,

N-1-cyclohexyl-N-2-[3-(p-tert-butylphenyl)-2-methylpropyl]-guanidine hydriodide, N-1-(2,2-dimethylcyclohexyl)-N-2-[3-(p-tert-butylphenyl)2-methylpropyl]-guanidine hydriodide, N-1-cyclohexyl-N-2-(p-tert-butylbenzyl)-guanidine hydrochloride, N-1-(3,3-dimethylcyclohex-Y1)-N-2-(p-tert-butylbenzyl)guanidine hydrochloride, N-1-cyclohexyl-N-2-[p-(2,3-dimethylbut-2-yl)-benzyl]-guanidine hydriodide, N-1-(p-tert-butylcyclohexyl)-N-2-(p-tert-butylbenz-yl)-N-3-methylguanidine hydriodide, N-1-cyclohexyl-N-2-n-butyl-N-3-(p-tert-butylbenzyl)-guanidine hydroacetate, N-1-cyclohexyl-N-2-(p-tert-butylbenzyl)-N-2-methylguanidine hydroacetate, N-1-(p-tert-butylbenzyl)-N-2-(2-ethylhexyl)-guanidine hydriodide, N-1-(p-tert-butylbenzyl)-N-2-(p-tert-butylbenzyl)-N3-methylguanidine hydriodide and 1-{[(3,3-dimethylcyclohexyl)-amino]-iminomethyl}-[3-(p-tert-butylphenyl)]-pyrrolidine.

The guanidines I are obtainable in various ways, preferably by the following methods:

(a) Preparation from thiuronium salts and amines

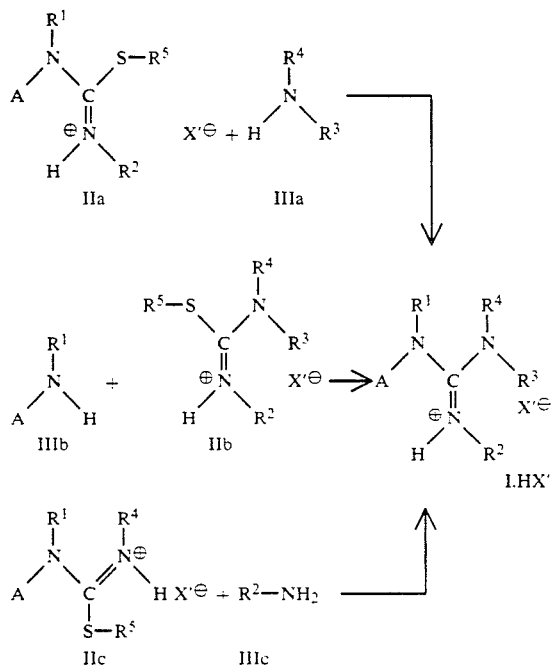

In these formulae, R[5] is benzyl or a short-chain alkyl radical, eg. methyl or ethyl, and X, is advantageously chloride, bromide, iodide, sulfate, methylsulfate, methylsulfonate or tosylate.

The starting compounds IIa-IIc and IIIa-IIIc are known or are obtainable in a known manner; regarding the thiuronium salts, reference may be made to Houben-Weyl, Methoden der Organischen Chemie, 4th edition, Vol. IX, page 900 et seq.

The reaction, known per se from Houben-Weyl, Methoden der Organischen Chemie, 4th edition, Vol. VIII, page 1893 et seq. and Vol. E4, page 614 et seq., of thiuronium salts with amines to give the guanidine derivatives I·HX' is preferably carried out in polar solvents such as alcohols, ketones, ethers, nitriles, dimethyl sulfoxide, N-methylpyrrolidone, dimethylformamide or dimethylacetamide.

The ratios of the reactants may be varied depending on the compounds used. Advantageously, equimolar amounts are reacted or, particularly preferably, twice the required amount of the amine component is used. Furthermore, a tertiary amine, such as triethylamine, may also be added as an auxiliary base to trap the mercaptan being formed. In this case, equimolar amounts, based on the thiuronium salt, of the auxiliary base are preferably used.

It is advisable to carry out the reactions at from 20° C. to the boiling point of the solvent, preferably from 60 to 130° C. Since the reactions are not pressuredependent, they are preferably carried out under atmospheric pressure.

By anion exchange, it is possible to obtain salts with other anions X⊖ or, in the case of exchange with hydroxyl ions, the free bases I.

(b) Preparation from aminoiminomethanesulfonic acids and amines

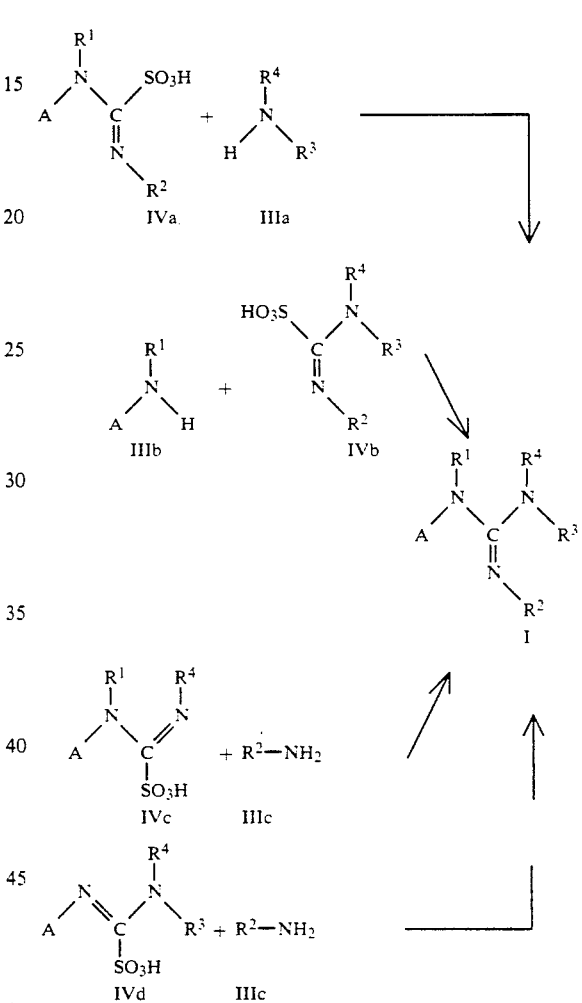

The starting compounds IVa-IVd are known or are obtainable in a known manner from thiourea derivatives (eg. C.A. Maryanoff et al., J. Org. Chem 51 (1986), 1982 et seq.).

The reaction, known per se from C.A. Maryanoff et al., loc. cit., of aminoiminosulfonic acids with amines to give the guanidine derivatives I is preferably carried out in a polar solvent, such as an alcohol or, particularly preferably, in acetonitrile.

It si advisable to carry out the reactions at from 0° C. to the boiling point of the solvent.

Regarding the ratios and the pressure, the data for Method (a) are applicable.

(c) Preparation from carbodiimides and amines

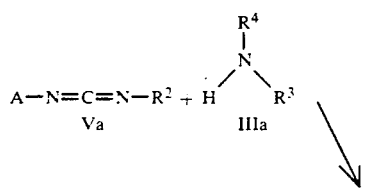

(d) Preparation from diphenylimidocarbonates and amines

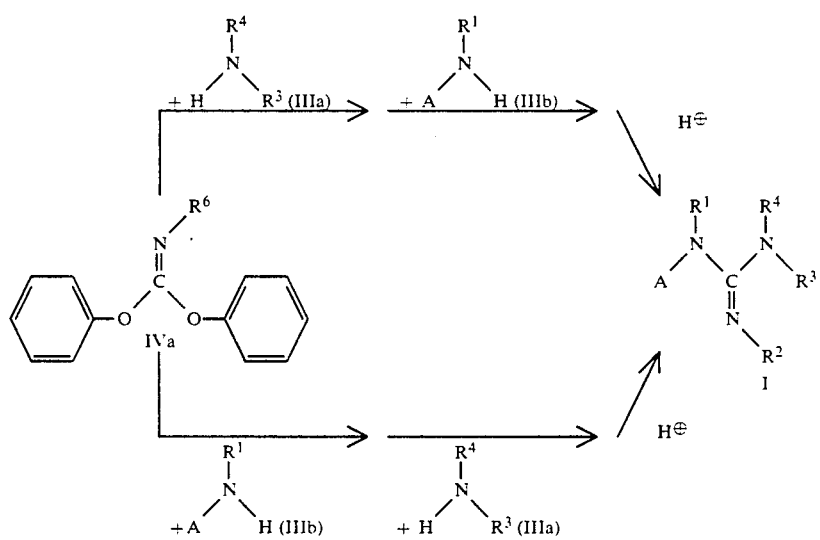

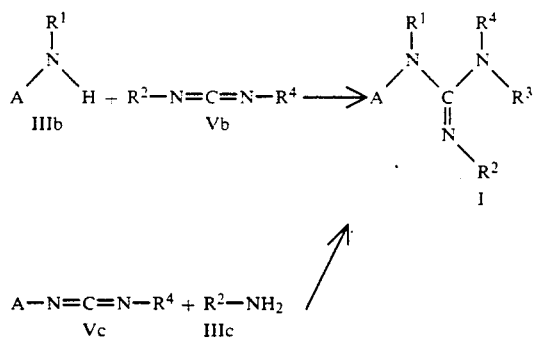

The starting compounds Va-Vc are known or are obtainable by known processes. By way of example, reference may be made to M. Mikolaiczyk, Tetrahedron 37 (1981), 233 et seq., Z.M. Jászay et al., Synthesis, 1987, et seq., and G. Appel et al., Chem. Ber. 104 (1971), 1335 et seq.

The reaction, known per se from Houben-Weyl, Methoden der Organischen Chemie, 4th edition, Vol. VIII, page 180 and Vol. E4, page 609, of carbodiimides with amines to give the guanidine derivatives I is preferably carried out in a nonpolar solvent, such as hexane, toluene, a short-chain alcohol, such as methanol or isopropanol, or a nitrile, such as acetonitrile.

For the reactions, it is advisable to use equimolar amounts of the starting compounds or, preferably, a small excess of the amine component, ie. not more than about 10%.

Regarding the temperature and the pressure, the data for Method (a) are applicable.

In formula IVa, $R^6$ is cyano, benzoyl or methanesulfonyl.

The reaction, known per se from A. Buschauer, Arzneim.-Forsch./Drug Res. 37 (II) (1987), 1003/1008 et seq., and Arch. Pharm. 321 (1988), 281, of diphenylimidodicarbonates with two amines is carried out in two separate stages. The reaction of the imidocarbonate with the first amine is preferably effected in a chlorohydrocarbon, such as methylene chloride, in ether, such as tetrahydrofuran or diethyl ether, or a nitrile, such as acetonitrile. The further reaction of the product with the second amine is carried out in a polar solvent, such as acetonitrile or pyridine.

Regarding the ratios, the temperature and the pressure, the data for Method (c) are applicable.

The hydrolysis of the resulting bases I where $R^2 = R^6$ is carried out in a known manner, advantageously in a mineral acid at, for example, from 70 to 120° C. Preferably, 2-12.5 M hydrochloric acid is used under reflux.

The chloride salts of the novel compounds I in which $R^2$ is hydrogen are obtained.

(e) Preparation from cyanogen bromide and amines

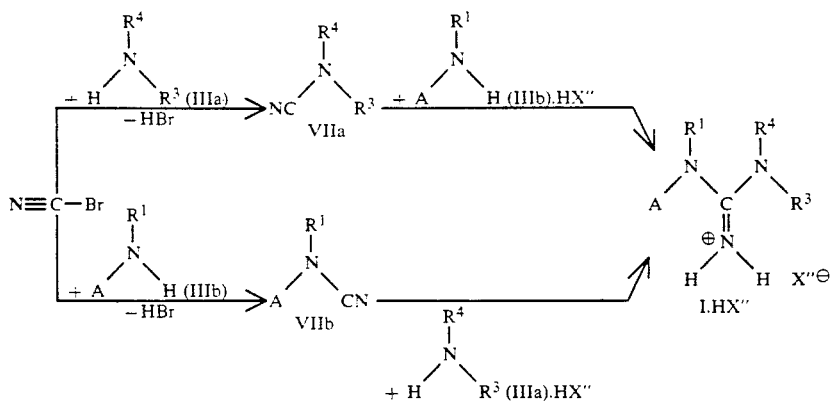

In these formulae, X" is preferably chloride.

The reaction, known per se from H.W. Geluk et al., J. Med. Chem. 12 (1969), 712 et seq., of cyanogen bromide with amines to give N-substituted cyanamide derivatives VIIa or VIIb is preferably carried out in an ether, such as diethyl ether or tetrahydrofuran.

An excess of the amine component over the cyanogen bromide, ie. not more than about 60%, is advantageously used.

It is advisable to carry out the reaction at from 0 to 25° C. Since the reactions are not pressuredependent, they are preferably effected under atmospheric pressure.

The reaction of the N-substituted cyanamides VIIa and VIIb with the hydrochlorides of the amines IIIb and IIIa is preferably carried out in the absence of a solvent, at, for example, from 150 to 250° C.

Regarding the amounts used, the pressure or the preparation of the free bases I, the data for Method c) are applicable.

The compounds of the formula I and their salts and metal complexes according to the definition are suitable as fungicides and are well tolerated by plants.

Generally speaking, the guanidines according to the invention are extremely effective on a broad spectrum of phytopathogenic fungi, in particular those from the Ascomycetes and Basidiomycetes classes. Some of them have a systemic action and can be used as foliar and soil fungicides.

The fungicidal compounds are of particular interest for controlling a large number of fungi in various crops or their seeds, especially wheat, rye, barley, oats, rice, Indian corn, lawns, cotton, soybeans, coffee, sugar cane, fruit and ornamentals in horticulture and viticulture, and in vegetables such as cucumbers, beans and cucurbits.

The novel compounds are particularly useful for controlling the following plant diseases:
Erysiphe graminis in cereals,
Erysiphe cichoracearum and Sphaerotheca fuliginea in cucurbits,
Podosphaera leucotricha in apples,
Uncinula necator in vines,
Puccinia species in cereals,
Rhizoctonia species in cotton and lawns,
Ustilago species in cereals and sugar cane,
Venturia inaequalis (scab) in apples,
Helminthosporium species in cereals,
Septoria nodorum in wheat,
Botrytis cinerea (gray mold) in strawberries and grapes,
Cerospora arachidicola in groundnuts,
Pseudocercosporella herpotrichoides in wheat and barley,
Pyricularia oryzae in rice,
Phytophthora infestans in potatoes and tomatoes,
Fursarium and Verticillium species in various plants,
Plasmopara viticola in grapes,
Alternaria species in vegetables and fruit.

The guanidines I are particularly suitable for combating *Botrytis cinerea*.

The compounds are applied by treating the plants, or the seed, materials or soil to be protected against fungus attack with a fungicidally effective amount of the active ingredients.

The novel substances can be converted into conventional formulations such as solutions, emulsions, suspensions, dusts, powders, pastes and granules. The application forms depend entirely on the purposes for which they are intended; they should at all events ensure a fine and uniform distribution of the active ingredient. The formulations are produced in known manner, for example by extending the active ingredient with solvents and/or carriers, with or without the use of emulsifiers and dispersants; if water is used as solvent, it is also possible to employ other organic solvents as auxiliary solvents. Suitable auxiliaries for this purpose are solvents such as aromatics (e.g., xylene), chlorinated aromatics (e.g., chlorobenzenes), praffins (e.g., crude oil fractions), alcohols (e.g., methanol, butanol), ketones (e.g., cyclohexanone), amines (e.g., ethanolamine, dimethylformamide), and water; carriers such as ground synthetic minerals (e.g., highly disperse silica and silicates); emulsifiers such as nonionic and anionic emulsifiers (e.g., polyoxyethylene fatty alcohol ethers, alkyl sulfonates and aryl sulfonates); and dispersants such as lignin-sulfite waste liquors and emthylcellulose.

The fungicidal agents generally contain from 0.1 to 95, and preferably from 0.5 to 90, wt% of active ingredient. The application rates are from 0.01 to 6, and especially from 0.02 to 3, kg of active ingredient per hectare, depending on the type of effect desired. The novel compounds may also be used for protecting materials (wood), for example against *Paecilomyces variotii*.

When the active ingredients are sued for treating seed, amounts of from 0.001 to 50, and preferably from 0.01 to 10, g per kg of seed are usually employed.

The agents and the ready-to-use formulations prepared from them, such as solutions, emulsions, suspensions, powders, dusts, pastes and granules, are applied in conventional manner, for example by spraying, atomizing, dusting, scattering, dressing or watering.

Examples of formulations are given below.

I. A solution of 90 parts by weight of compound no. 3a and 10 parts by weight of N-methyl-α-pyrrolidone, which is suitable for application in the form of very fine drops.

II. A mixture of 20 parts by weight of compound no. 2a 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil; by finely distributing the solution in water a dispersion is obtained.

III. An aqueous dispersion of 20 parts by weight of compound no. 5a, 40 parts by weight of cyclohexanone, 30 parts by weight of isobutanol, 20 parts by weight of the adduct of 40 moles of ethylene oxide and 1 mole of castor oil.

IV. An aqueous dispersion of 20 parts by weight of compound no. 26a, 25 parts by weight of cyclohexanol, 65 parts by weight of a mineral oil fraction having a boiling point between 210 and 280° C., and 10 parts by weight of the adduct of 40 moles of ethylene oxide and 1 mole of castor oil.

V. A mixture, triturated in a hammer mill, of 80 parts by weight of compound no. 37a, 3 parts by weight of the sodium salt of diisobutylnapthalene-α-sulfonic acid, 10 parts by weight of the sodium salt of a lignin-sulfonic acid obtained from a sulfite waste liquor, and 7 parts by weight of powdered silica gel; by finely distributing the mixture in water, a spray liquor is obtained.

VI. An intimate mixture of 3 parts by weight of compound no. 1b and 97 parts by weight of particulate kaolin. This dust contains 3% by weight of the active ingredient.

VII. An intimate mixture of 30 parts by weight of compound no. 2b, 92 parts by weight of powdered silica gel and 8 parts by weight of paraffin oil sprayed onto the surface of this silica gel; this formulation of the active ingredient has good adherence.

VIII. A stable aqueous dispersion of 40 parts by weight of compound no. 4b, 10 parts by weight of the sodium salt of a phenolsulfonic acid-urea-formaldehyde condensate, 2 parts of silica gel and 48 parts of water; this dispersion can be further diluted.

IX. A stable oily dispersion of 20 parts by weight of compound no. 9b, 2 parts by weight of the calcium slat of dodecylbenzenesulfonic acid, 8 parts by weight of a fatty alcohol polyglycol ether, 2 parts by weight of the sodium salt of a pheolsulfonic acid-urea-formaldehyde condensate and 68 parts by weight of a paraffinic mineral oil.

In these applications forms, the agents according to the invention may also be present together with other active ingredients, for example herbicides, insecticides, growth regulators, and fungicides, and may furthermore be mixed and applied together with fertilizers. Admixture with other fungicides frequently results in an increase in the fungicidal spectrum.

MANUFACTURING EXAMPLES

Example A, according to method (a) (compound 7b in table)

N-1-(4-tert.-butylbenzyl)-N-2-methyl-N-3-(3,5,5-trimethyl-hexyl)-guanidine hydroiodide

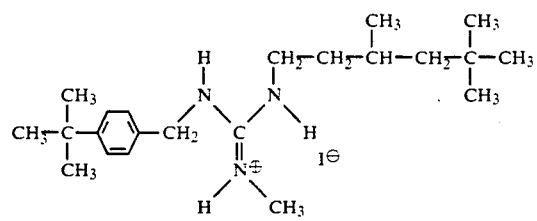

Under a nitrogen blanket, a mixture of 19 g (0.05 mol) of N-(4-tert.-butylbenzyl)-N'-, S-dimethylisothiuronium iodide, 14.1 g (0.1 mol) of 3,5,5-trimethylhexylamine, 5 g (0.05 mol) of triethylamine and 20 g of molecular sieve (4A) in 200 ml of anhydrous acetonitrile was refluxed for 6 hours with elimination of methanethio. After filtration while hot, the mixture was worked up in the usual manner.

Yield: 64% of theory; m.p. 165° C.

Intermediate state A1

N-(4-tert.-Butylbenzyl)-N'-methylthiourea

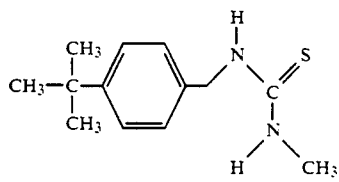

At 20 to 30° c., a solution of 163 g (1 mol) of 4-tert.-butylbenzylamine in 100 ml of anhydrous acetonitrile was dripped, while cooling, into a mixture of 73 g (1 mol) of methyl isothiocyanate in 80 ml of anhydrous acetonitrile. The mixture was stirred for 3 hours at 20° C. and then for a further hour at 80 to 90° C. before being evaporated down. The crude product was precipitated with hexane from ethyl acetate, washed with hexane and dried under reduced pressure at 60° c.

Yield: 72% of theory; mp 72° C.

Intermediate state A2

N-(4-tert-Butylbenzyl)-N'-S-dimethylisothiuronium iodide

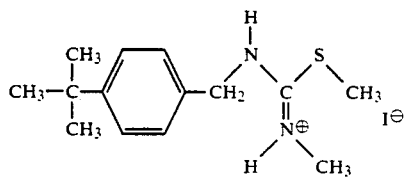

A solution of 23.6 g (0.1 mol) of N-(4-tert.-butylbenzyl)-N'-methylthiourea and 114.2 g (0.1 mol) of iodomethane in 200 ml of methanol was reluxed for one hour. After the mixture had cooled to room temperature the product was precipitated by adding methyl tert-butyl ether, washed and dried under reduced pressure at 40° C.

Yield: 53% of theory; mp: 172° C.

Example B, according to method (a) (compound 20b in table)

N-1-(4-tert.-Butylbenzyl)-N-2-n-octylguanidin hydroiodide

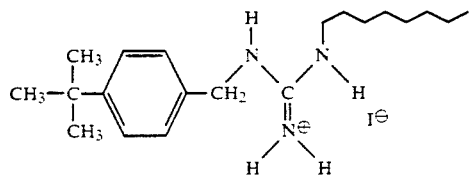

A mixture of 9.1 g (2,5·10$^{-2}$ mol) of N-(4-tert.-butylbenzyl)-S-methylisothiuronium iodide, 6.5 g (5·10$^{-2}$ mol) of n-octylamine, 2.5 g (25 mmol) of trithylamine, 3 g of molecular sieve (4 A) and 200 ml of acetonitrile was refluxed for 48 hours and worked up as described in Example A.

Yield: 61% of theory; mp.: 113° C.

Intermediate stage B1

N-(4-tert.-Butylbenzyl)-thioure

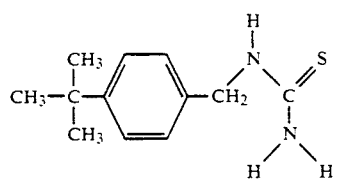

Over a period of 10 minutes, a solution of 147.5 g (1.05 mol) of benzoyl chloride was dripped into a solution of 82.5 g (1.1 mol) of ammonium thiocyanate in 300 ml of absolute acetone. After the mixture had been stirred for 10 minutes at the reflux temperature, a solution of 163 g (1 mol) of 4-tert.-butylbenzylamine in 150 ml of acetone was dripped in, and the reaction mixture was reluxed for 20 minutes and stirred into 2 liters of ice water. The precipitated solid was washed with water, dissolved in a hot mixture of 1 liter of 10% strength caustic solution and 550 ml of ethanol and refluxed for a further 15 minutes.

The mixture was then diluted with ice water, adjusted with concentrated hydrochloric acid to a pH of 1 and then with solid sodium bicarbonate to a pH of about 9. The resulting precipitate was washed with water and dried under reduced pressure at 60° C.

Yield: 92% of theory; mp.:80° C.

Intermediate state B2

N-(4-tert.-Butylbenzyl)-S-methylisothiuronium iodide

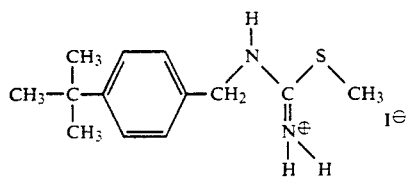

At 30 to 40° C., 54.5 g (0.333 mol) of iodomethane was dripped into 85 g (0.383 mol) of N-(4-tert.-butylbezyl)-thiourea in 200 ml of methanol. The mixture was reacted and worked up analogously to Example A, intermediate state A2; the product was dired at 60° C.

Yield: 74% of theory; mp.: 143° C.

Example C, according to method (a) (example 1a in table)

N-1-Cyclohexyl-N-2-(4-tert.-butylbenzyl)-guanidine hydroiodide

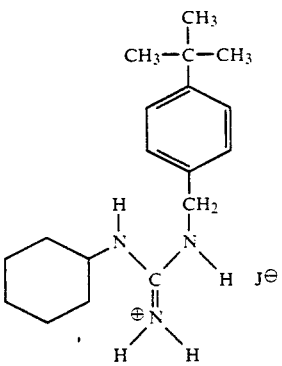

30 g (0.1 mol) of N-cyclohexyl-S-methylisothiuronium iodide, 32.6 g (0.2 mol) of 4-tert.-butylbenzylamine, 10.1 g (0.1 mol) of triethylamine and 3 g of molecular sieve (4 A) were reacted for 48 hours in 200 ml of anhydrous acetonitrile analogously to Example A.

Yield: 95% of theory; mp.: 145-150° C.

Example D, according to method (a) (example 41a in table)

N-1-(3-methyl-cyclohexyl)-N-2-(4-tert.-butylbezyl)-N-3-methylguanidine hydroiodide

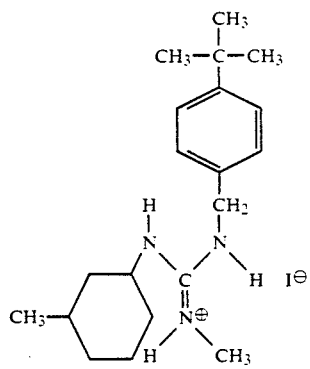

9.5 g (25 mmol) of N-(4-tert.-butylbenzyl)-N',S-dimethylisothiuronium iodide, 5.7 g (50 mmol) of 3-methylcyclohexylamine (isomer mixture), 2.5 g (25 mmol) of triethylamine and 1.5 g of molecular sieve (4 A) in 100 ml of acetonitrile were reacted for 2 hours analogously to Example A.

Yield: 25% of theory; mp.: 150° C.

Example E, according to method (c) (example 11 b in table)

N-1-(4-tert.-Butylbenzyl)-N-2-n-butyl-N-3-(2,2-dimethylpropyl)-guanidine hydrochloride

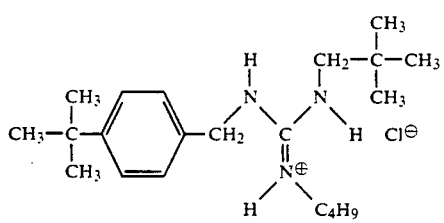

A mixture of 2 g (8,2·10⁻³ mol) of N-(4-tert.-butylbenzyl)-N'-n-butyl-carbodiimide, 0.17 g (8,2·10⁻³ mol) of 2,2-dimethylpropylamine and 100 ml of anhydrous tert.-butanol was refluxed for 24 hours. An oily product was isolated, methanolic hydrochloric acid was added, and the mixture was concentrated under reduced pressure and crystallized by trituration with methyl tert.-butyl ether.

Yield: 33% of theory; mp.: 88° C.

Example F, according to method (c) (example 57a in table)

N-1-(4-tert.-butyl-cyclohexyl)-N-2-n-butyl-N-3-(4-tert.-butylbenyl)-guanidin hydrochloride

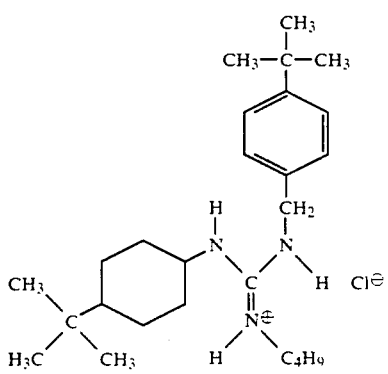

2 g (8,2·10⁻³ mol) of N-(4-tert.-butylbenzyl)-N'-n-butylcarbodiimide and 1.27 g (8,2·10³ mol) of 4-tert.-butylcyclohexylamine were reacted analogously to Example E.

Yield: 30% of theory; mp.: 110° C.

Example G (example 30a in table)

N-1-cyclohexyl-N-2-[3-(4-tert.-butylphenyl)-2-methylpropyl]-guanidine hydrochloride

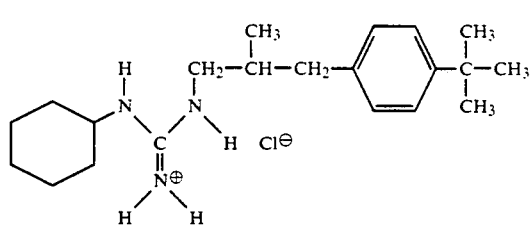

21.8 g (6,6·10⁻² mol) of N-1-cyclohexyl-N-2-[3-(4-tert.-butylphenyl)-2-methylpropyl]guanidine hydroiodide (example 26a from Table 1) in 300 of methanol/water (1:1) were filtered through a column containing 250 g of Amberlyst A 26 (OH⊖ form). After working up, the free guanidine obtained was converted into the hydrochloride with an excess of methanolic hydrochloric acid.

Yield: 80%; mp.: 169° C.

The compounds listed in Table 1 below were obtained analogously to Examples A to G:

TABLE 1

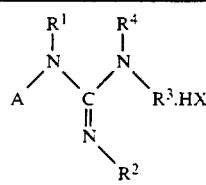

| Comp. No. | A | $R^1$ | $R^2$ | $R^3$ | $R^4$ | HX | mp./IR (film)[cm⁻¹] |
|---|---|---|---|---|---|---|---|
| 1a | cyclohexyl | H | H | H | 4-tert.-butylbenzyl | HI | 145° C. |
| 2a | cyclohexyl | H | CH₃ | H | 4-tert.-butylbenzyl | HI | 180° C. |
| 3a | cyclohexyl | H | H | CH₃ | 4-tert.-butylbenzyl | HI | 140° C. |
| 4a | cyclohexyl | CH₃ | H | H | 4-tert.-butylbenzyl | HI | 152° C. |
| 5a | cyclohexyl | H | H | H | 4-tert.-butylbenzyl | HCl | 195° C. |
| 6a | cyclohexyl | H | H | H | 4-tert.-butylbenzyl | CH₃COOH | 195° C. |
| 7a | cyclohexyl | H | H | H | 4-tert.-butylbenzyl | (COOH)₂ | 1719, 1703, 1615, 1515, 1445, 1403, 1230, 1202, 1173, 721 |
| 8a | cyclohexyl | H | CH₃ | H | 4-tert.-butylbenzyl | CH₃COOH | 2930, 2854, 1586, 1514, 1463, 1450, 1393, 1364 |
| 9a | cyclohexyl | H | CH₃ | H | 4-tert.-butylbenzyl | HCl | 3253, 3200, 3102, 2932, 2856, 1625, 1451, 1366, |

TABLE 1-continued

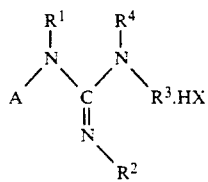

| Comp. No. | A | R¹ | R² | R³ | R⁴ | HX | mp./IR (film)[cm⁻¹] |
|---|---|---|---|---|---|---|---|
| 10a | cyclohexyl | H | H | CH₃ | 4-tert.-butylbenzyl | — | 1347, 1174 2936, 1652, 1606, 1487, 1398, 1094, 1072, 1007 |
| 11a | cyclohexyl | H | H | CH₃ | 4-tert.-butylbenzyl | HCl | 140° C. |
| 12a | cyclohexyl | H | H | CH₃ | 4-tert.-butylbenzyl | CH₃COOH | 2962, 2862, 2856, 1667, 1613, 1567, 1514, 1397 |
| 13a | cyclohexyl | H | H | CH₃ | 4-tert.-butylbenzyl | (COOH)₂ | 140° C. |
| 14a | cyclohexyl | H | n-butyl | H | 4-tert.-butylbenzyl | — | 2957, 2929, 2854, 1634, 1512, 1449 |
| 15a | cyclohexyl | H | n-butyl | H | 4-tert.-butylbenzyl | HCl | 105° C. |
| 16a | cyclohexyl | H | n-butyl | H | 4-tert.-butylbenzyl | CH₃COOH | resin |
| 17a | cyclohexyl | H | H | H | 4-tert.-butylbenzyl | — | 3277, 3179, 2960, 2931, 2854, 1647, 1626 |
| 18a | cyclohexyl | H | H | H | 4-tert.-butylbenzyl | HI | 128° C. |
| 19a | cyclohexyl | H | H | H | 4-tert.-butylbenzyl | CH₃COOH | |
| 20a | cyclohexyl | H | H | CH₃ | 4-tert.-butylbenzyl | — | |
| 21a | cyclohexyl | H | H | CH₃ | 4-tert.-butylbenzyl | HI | |
| 22a | cyclohexyl | H | H | CH₃ | 4-tert.-butylbenzyl | CH₃COOH | |
| 23a | cyclohexyl | H | CH₃ | H | 4-tert.-butylbenzyl | — | |
| 24a | cyclohexyl | H | CH₃ | H | 4-tert.-butylbenzyl | HI | |
| 25a | cyclohexyl | H | CH₃ | H | 4-tert.-butylbenzyl | CH₃COOH | |
| 26a | cyclohexyl | H | H | H | 3-(4-tert.-butylphenyl)-2-methylpropyl | HI | 80° C. |
| 27a | cyclohexyl | H | H | H | 4-(2,3-dimethylbut-2-yl)-benzyl | HI | >200° C. |
| 28a | cyclohexyl | H | H | H | n-tridecyl | HI | 3283, 3252, 3181, 2926, 2854, 1646, 1631, 1466, 1452, 1369 |
| 29a | cyclohexyl | H | H | H | 6,10-dimethylundec-2-yl | HI | 3268, 3185, 2928, 2855, 1667, 1646, 1624, 1451 |
| 30a | cyclohexyl | H | H | H | 3-(4-tert.-butylphenyl)-2-methylpropyl | HCl | 169° C. |
| 31a | cyclohexyl | H | H | H | 3-(4-tert.-butylphenyl)-2-methylpropyl | ½(COOH)₂ | 110° C. |
| 32a | cyclohexyl | H | H | H | 3-(4-tert.-butylphenyl)-2-methylpropyl | CH₃COOH | 3020, 2959, 2931, 2857, 1648, 1558, 1403, 1363 |
| 33a | cyclohexyl | H | n-butyl | H | benzyl | CH₃COOH | 2932, 2856, 1625, 1596, 1569, 1496, 1452, 1399, 1377, 1253 |
| 34a | cyclohexyl | H | H | H | 4-tert.-butylbenzyl | — | 145° C. |
| 35a | cyclopentyl | H | H | CH₃ | 4-tert.-butylbenzyl | — | |
| 36a | cyclopentyl | H | CH₃ | H | 4-tert.-butylbenzyl | HI | 145° C. |
| 37a | cyclooctyl | H | CH₃ | H | 4-tert.-butylbenzyl | HI | 82° C. |
| 38a | cyclooctyl | H | H | CH₃ | 4-tert.-butylbenzyl | — | |
| 39a | cyclododecyl | H | CH₃ | H | 4-tert.-butylbenzyl | HI | 124° C. |
| 40a | cyclododecyl | H | H | H | 4-tert.-butylbenzyl | HI | 170° C. |
| 41a | 3-methyl-cyclohexyl | H | CH₃ | H | 4-tert.-butylbenzyl | HI | 150° C. |
| 42a | 4-tert.-butyl-cyclohexyl | H | CH₃ | H | 4-tert.-butylbenzyl | HI | 220° C. |
| 43a | 4-tert.-butyl-cyclohexyl | H | H | H | 4-tert.-butylbenzyl | HI | 200° C. |
| 44a | 4-tert.-butyl-cyclohexyl | H | H | H | 4-tert.-butyloxybenzyl | HI | 206° C. |
| 45a | 4-isopropyl-cyclohexyl | H | CH₃ | H | 4-tert.-butylbenzyl | HI | 2959, 2933, 2867, 1634, 1513, 1366 |
| 46a | 4-isopropyl-cyclohexyl | H | H | H | 4-tert.-butyloxybenzyl | HI | |
| 47a | 3,3-dimethyl-cyclohexyl | H | H | H | 4-tert.-butylbenzyl | HI | 180° C. |
| 48a | 3,3-dimethyl-cyclohexyl | H | H | H | 4-tert.-butyloxybenzyl | — | |
| 49a | 3,3-dimethyl-cyclohexyl | H | H | H | 3-(4-tert-butylphenyl)-2-methyl-propyl | HI | 110° C. |
| 50a | 3-trifluoro-methylcyclohexyl | H | H | H | 4-tert.-butylbenzyl | HI | 90° C. |
| 51a | 3-trifluoro-methylcyclohexyl | H | H | H | 4-tert.-butyloxybenzyl | — | |
| 52a | 3-trifluoro-methylcyclohexyl | H | H | H | 3-(4-tert-butylphenyl)-2-methylpropyl | HI | 95° C. |

TABLE 1-continued

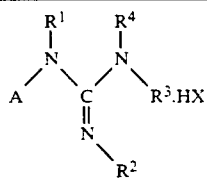

| Comp. No. | A | R¹ | R² | R³ | R⁴ | HX | mp./IR (film)[cm⁻¹] |
|---|---|---|---|---|---|---|---|
| 53a | 3,3-dimethyl-cyclohexyl | H | H | H | 4-tert.-butylbenzyl | HCl | >200° C. |
| 54a | 3,3-dimethyl-cyclohexyl | H | H | H | 4-tert.-butylbenzyl | CH₃COOH | 120° C. |
| 55a | 3,3-dimethyl-cyclohexyl | H | H | H | 4-tert.-butylbenzyl | (COOH)₂ | 155° C. |
| 56a | 4-tert.-butyl-cyclohexyl | H | n-butyl | H | 4-tert.-butylbenzyl | CH₃COOH | 2959, 2866, 1629, 1572, 1515, 1393, 1366 |
| 57a | 4-tert.-butyl-cyclohexyl | H | n-butyl | H | 4-tert.-butylbenzyl | HCl | 110° C. |
| 58a | 3-methyl-cyclohexyl | H | n-butyl | H | 4-tert.-butylbenzyl | HCl | 75° C. |
| 59a | 3-methyl-cyclohexyl | H | n-butyl | H | 4-tert.-butylbenzyl | CH₃COOH | 2957, 2929, 2869, 1628, 1571, 1515, 1458, 1394, 1367, 1268 |
| 60a | 3-methyl-cyclohexyl | H | H | H | 4-tert.-butylbenzyl | HI | 100° C. |
| 61a | 2-methyl-cyclohexyl | H | CH₃ | H | 4-tert.-butylbenzyl | HI | 102° C. |
| 62a | cyclohexyl | H | isopropyl | H | 4-tert.-butylbenzyl | HCl | 135° C. |
| 63a | cyclohexyl | H | but-2-yl | H | 4-tert.-butylbenzyl | HCl | 105° C. |
| 64a | cyclohexyl | H | H | H | 4-chlorobenzyl | HI | 80° C. |
| 65a | cyclohexyl | H | H | H | 2,4-dichlorobenzyl | HI | 3270, 3274, 2931, 1648, 1624, 1589, 1563, 1544 |
| 66a | cyclohexyl | H | H | H | 4-cyanobenzyl | — | |
| 67a | cyclohexyl | H | H | H | 4-trifluoromethylbenzyl | — | |
| 68a | cyclohexyl | H | H | H | 1-phenyl-ethyl | — | |
| 69a | cyclohexyl | H | H | R³ + R⁴ = 3-(4-tert.-butyl-phenyl)-pyrroidinyl | | HI | 195° C. |
| 70a | cyclohexyl | H | H | R³ + R⁴ = 3-(6-methylhept-2-yl)-pyrrolidinyl | | HI | 135° C. |
| 71a | 3,3-dimethyl-cyclohexyl | H | H | R³ + R⁴ = 3-(4-tert.butyl-phenyl)-pyrrolidinyl | | HI | 170° C. |
| 72a | cyclohexyl | H | H | R³ + R⁴ = 4-isopropyl-piperidinyl | | HI | 169° C. |
| 73a | cyclohexyl | H | H | R³ + R⁴ = 3-(6-methylhept-2-yl)-pyrrolidinyl | | HI | 110° C. |
| 74a | cyclohexyl | H | H | R³ + R⁴ = 3-(6-methylhept-2-yl)-pyrrolidinyl | | CH₃COOH | 3272, 3165, 2931, 2859, 1660, 1617, 1557, 1468, 1452, 1383 |
| 75a | cyclohexyl | H | H | R³ + R⁴ = 3-(6-methylhept-2-yl)-pyrrolidinyl | | (COOH)₂ | 3200, 2932, 2859, 1738, 1647, 1620, 1553, 1467, 1452, 1205 |
| 76a | cyclohexyl | H | H | R³ + R⁴ = (2,4,4-trimethyl-pentyl)-pyrrolidinyl | | HI | 175° C. |
| 77a | 4-tert.-butyl-cyclohexyl | H | H | H | 3-(4-tert.-butylpenyl)-2-methylpropyl | — | |
| 78a | 4-(2,4,4-tri-methylhex-2-yl)-cyclohexyl | H | H | H | 4-tert.-butylbenzyl | HI | 100° C. |
| 79a | 4-(2,4,4-tri-methylhex-2-yl)-cyclohexyl | H | H | H | 3-(4-tert-butylphenyl)-2-methylpropyl | — | |
| 80a | 4-ethoxy-cyclohexyl | H | H | H | 4-tert.butylbenzyl | — | |
| 81a | 4-hydroxyethyl-cyclohexyl | H | H | H | 4-tert.-butylbenzyl | — | |
| 82a | 4-chlorocyclo-hexyl | H | H | H | 4-tert.-butylbenzyl | — | |
| 83a | 4-tert.-buto-oxycyclohexyl | H | H | H | 4-tert.-butylbenzyl | — | |
| 84a | 4-tert.-buto-oxycyclohexyl | H | H | H | 4-tert.-butyloxybenzyl | — | |
| 85a | 3,3,5-tri-methylcyclohexyl | H | H | H | 4-tert.-butyloxybenzyl | — | |
| 86a | 3,3,5-tri-methylcyclohexyl | H | H | H | 4-tert.-butyloxybenzyl | — | |
| 87a | 4-chloroethyl-cyclohexyl | H | H | H | 4-tert.-butyloxybenzyl | — | |
| 88a | 4-chloroethyl- | H | H | H | 4-tert.-butyloxybenzyl | — | |

TABLE 1-continued

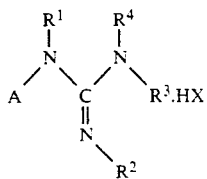

| Comp. No. | A | R¹ | R² | R³ | R⁴ | HX | mp./IR (film)[cm⁻¹] |
|---|---|---|---|---|---|---|---|
| 89a | cyclohexyl | H | H | H | 4-hydroxybenzyl | — | |
| 90a | cyclohexyl | H | H | H | 4-trichoromethylbenzyl | — | |
| 91a | cyclohexyl | H | H | H | 4-methoxybenzyl | HI | 48° C. |
| 92a | cyclohexyl | H | H | H | 2-(4-methoxyphenyl)ethyl | HI | 3249, 3179, 2932, 1647, 1629, 1513, 1247 |
| 93a | cyclohexyl | H | H | H | C₁₃H₂₇(isomer mixture) | — | |
| 94a | cyclohexyl | H | H | H | cyclohexylmethyl | — | |
| 95a | cyclohexyl | H | H | H | 2,2-dimethylpropyl | — | |
| 96a | cyclohexyl | H | H | H | n-hexyl | — | |
| 97a | cyclohexyl | H | H | H | n-octyl | HI | 3285, 3250, 3181, 2929, 2855, 1647, 1631, 1602 |
| 98a | cyclohexyl | H | H | H | 3-methyl-butyl | — | |
| 99a | cyclohexyl | H | H | H | phenethyl | — | |
| 100a | cyclohexyl | H | H | H | 2-ethylhexyl | HI | 3284, 3252, 3181, 2958, 2930, 2857, 1647, 1630 |
| 101a | cyclohexyl | H | H | H | 6-ethyl-4-oxadecyl | — | |
| 102a | cyclohexyl | H | H | H | 4-tert.-butyl-phenylpropyl | — | |
| 103a | cyclohexyl | H | H | H | 3-tert.-butylbenzyl | — | |
| 104a | 2-hydroxy-1,1-dimethyl-ethyl-cyclohexyl | H | H | H | 4-tert.-butylbenzyl | — | |
| 105a | cyclohexyl | H | H | H | 4-isopropylbenzyl | — | |
| 106a | cyclohexyl | H | H | H | 4-(2,4,4-trimethyl-pentyl)benzyl | — | |
| 107a | 4-tert.-butyl-cyclohexyl | H | H | H | 4-tert.-amylbenzyl | — | |
| 108a | 1-methoxy-1-methylethyl-cyclhexyl | H | H | H | 4-tert.-butyoxybenzyl | — | |
| 109a | cyclohexyl | H | H | H | 4-(1-methoxy-1-methyl-ethyl)benzyl | — | |
| 110a | cyclohexyl | H | H | H | 4(1-hydroxy-1-methyl-ethyl)benzyl | — | |
| 111a | cyclohexyl | H | H | H | 4-isopropenyl-benzyl | — | |
| 112a | cyclohexyl | H | H | H | 4-n-butoxy-benzyl | — | |
| 113a | 4-tert.-amyl-cyclohexyl | H | H | H | 4-tert.-butylbenzyl | — | |
| 114a | cyclohexyl | H | H | H | 2-methyl-4-tert.-butyl-benzyl | — | |
| 115a | cyclohexyl | H | H | H | 3,5,5-trimethylhexyl | — | |
| 116a | cyclohexyl | H | H | H | 6,10,14-trimethyl-pentadec-2-yl | HI | 3273, 3183, 2927, 2855, 1647, 1624, 1597, 1533 |
| 117a | cyclohexyl | H | H | H | 4-(4-tert.-butoxy-phenyl)-but-2-yl | HI | 2974, 2930, 1608, 1450, 1365, 1161 |
| 118a | cyclohexyl | H | H | H | 2-(4-tert.-butyl-phenyl)-ethyl | HI | 3291, 3220, 3173, 2965, 2952, 2931, 1640, 1633 |
| 119a | cyclohexyl | H | H | H | 3-chlorobenzyl | HI | 3249, 3178, 2931, 2854, 1647, 1625, 1597, 1576 |
| 120a | cyclohexyl | H | H | H | 5-methyl-oct-2-yl | — | |
| 121a | cyclohexyl | H | H | H | 2,4,5-trimethoxybenzyl | — | |
| 122a | cyclohexyl | H | H | H | 4-methoxybenzyl | — | |
| 123a | 4-(1-methoxy-1-methyl)ethyl-cyclohexyl | H | H | H | 4-tert.-butylcyclohexyl | — | |
| 124a | cyclohexyl | H | H | H | 3-(4-tert.-butylphenyl)-2-methylpropyl | — | 2958, 2928, 2854, 1615, 1570, 1510, 1450, 1363 |
| 125a | cyclohexyl | H | H | R³ + R⁴ = | 3-(6-methylhept-2-yl)-pyrrolidinyl | — | 2952, 2926, 2853, 1591, 1542, 1518, 1449, 1364 |
| 126a | cyclohexyl | H | H | H | benzyl | HI | 134° C. |
| 127a | cyclohexyl | H | H | H | n-undecyl | HI | 3283, 3251, 3182, 2927, 2854, 1647, 1630, 1452 |
| 128a | cyclohexyl | H | H | H | n-tetradecyl | HI | 3251, 3180, 2925, 2854, 1648, 1631 |
| 129a | cyclohexyl | H | H | H | oct-2-yl | HI | 3275, 3182, 2929, 2855, 1647, 1624, 1600, 1553 |
| 130a | cyclohexyl | H | H | H | 4-phenylbutyl | HI | 3277, 3182, 3084, 2932, 2856, 1648, 1630, 1452 |
| 131a | cyclohexyl | H | H | R³ + R⁴ = | 4-(2,6-dimethyl)- | HI | 150° C. |

TABLE 1-continued

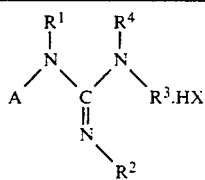

| Comp. No. | A | R¹ | R² | R³ | R⁴ | HX | mp./IR (film)[cm⁻¹] |
|---|---|---|---|---|---|---|---|
| 132a | cyclohexyl | H | H | H | morpholinyl n-dodecanyl | HI | 3248, 3180, 2924, 2853, 1647, 1631 |
| 133a | cyclohexyl | H | H | H | 2,3-dimethoxy-benzyl | HI | 178° C. |
| 134a | cyclohexyl | H | H | H | 4-bromobenzyl | HI | 3369, 3312, 3246, 3188, 2931, 1651, 1624, 1489 |
| 135a | cyclohexyl | H | H | R³ + R⁴ = | 3-methyl-4-(4-tert.-butylphenyl)-pyrrolidinyl | HI | 128° C. |
| 136a | cyclohexyl | H | H | H | 3,4-dichlorobenzyl | HI | 3281, 3179, 2930, 1648, 1624, 1470 |
| 137a | cyclohexyl | H | H | H | 2-chlorobenzyl | HI | 3248, 3174, 2930, 2854, 1646, 1625, 1444 |
| 138a | cyclohexyl | H | H | R³ + R⁴ = | 4-(4-tert-butylphenyl)-piperidinyl | HI | 205° C. |
| 139a | cyclohexyl | H | H | CH₃ | 2,5,7,7-tetramethyl-octyl | HI | 3300, 3194, 3166, 2950 2932, 1638, 1616, 1544 |
| 140a | cyclohexyl | H | H | H | 4-(1,1,3,3-tetramethyl-butyl)-benzyl | HI | 75° C. |
| 141a | cyclohexyl | H | H | H | n-pentyl | HI | 3281, 3250, 3182, 2930, 2856, 1646, 1629, 1600 |
| 142a | cyclohexyl | H | H | H | 4-tert.-butylbenzyl | H₃BO₃ | 72° C. |
| 143a | cyclohexyl | H | H | H | 4-tert.-butylbenzyl | acetyl acetonate | 3282, 3184, 2932, 2855, 1646, 1629, 1451 |
| 144a | cyclohexyl | H | H | H | 4-tert.-butylbeznyl | o-hydroxy-phenol | 52° C. |
| 145a | cyclohexyl | H | H | H | 4-tert.-butylbenzyl | C₆H₅—COOH | 70° C. |
| 146a | cyclohexyl | H | H | H | 4-tert.-butylbenzyl | CCl₃—COOH | 3317, 3197, 2935, 2859, 1659, 1633, 1324, 832 |
| 147a | cyclohexyl | H | H | H | 4-tert.-butylbenzyl | 3,4,5-(OH)₃—C₆H₅—COOH | 125° C. |
| 148a | cyclohexyl | H | H | H | 4-tert.-butylbenzyl | H₂CO₃ | 87° C. |
| 149a | cyclohexyl | H | H | H | 4-(1,1,2-trimethyl-propyl)-benzyl | HCl | 180° c. |
| 150a | cyclohexyl | H | H | H | 4-(1,1,2-trimethyl-propyl)-benzyl | CH₃COOH | 250° C. |
| 151a | cyclohexyl | H | H | H | 4-(1,1,2-trimethyl-propyl)-benzyl | C₂H₂O₄ | 75° C. |
| 152a | cyclohexyl | H | H | H | n-tridecyl | HCl | 120° C. |
| 153a | cyclohexyl | H | H | H | n-tridecyl | CH₃COOH | 3173, 2925, 2853, 1651, 1569, 1465, 1452, 1404 |
| 154a | cyclohexyl | H | H | H | n-tridecyl | C₂H₂O₄ | 3299, 3191, 2925, 2853, 1636, 1465, 1453, 1218, 720 |
| 155a | cyclohexyl | H | H | H | 6,10-dimethyl-undec-2-yl | HCl | 120° C. |
| 156a | cyclohexyl | H | H | H | 6,10-dimethyl-undec-2-yl | CH₃COOH | 3272, 3175, 2928, 2856, 1571, 1450, 1402, 1014 |
| 157a | cyclohexyl | H | H | H | 6,10-dimethyl-undec-2-yl | C₂H₂O₄ | 3272, 3189, 2929, 1628, 1603, 1403, 1191, 720 |
| 158a | 4-tert.-butyl-cyclohexyl | H | n-butyl | H | 4-tert.-butylbenzyl | — | 2958, 2862, 1636, 1512, 1365 |
| 159a | 4-tert.-butyl-cyclohexyl | H | H | R³ + R⁴ = | 2-methyl-3-(4-tert.-butylphenyl)-pyrrolidinyl | HI | 245° C. |
| 160a | 4-tert.-butyl-cyclohexyl | H | H | H | 3-(morpholin-4-yl)-prop-1-yl | HI | 3276, 3186, 2947, 2860, 1630, 1450, 1141, 1116 |
| 161a | 4-tert.-butyl-cyclohexyl | H | H | CH₃ | 2,5,7,7-tetramethyl-octyl | HI | 202° C. |
| 162a | 4-tert.-butyl-cyclohexyl | H | H | H | 2,4-dicholorobenzyl | HI | 163° C. |
| 163a | 4-tert.-butyl-cyclohexyl | H | H | H | 4-tert.-butylbenzyl | HCl | 162° C. |
| 164a | 4-tert.-butyl-cyclohexyl | H | H | H | 4-tert.-butylbenzyl | CH₃COOH | 170° C. |
| 165a | 4-tert.-butyl-cyclohexyl | H | H | H | 4-tert.-butylbenzyl | C₂H₂O₄ | 102° C. |
| 166a | 3-methyl-cyclohexyl | H | n-butyl | H | 4-tert.-butylbenzyl | — | 2955, 2925, 2867, 1636, 1512, 1458 |
| 167a | 2-methyl-cyclohexyl | H | H | H | 4-tert.-butylbenzyl | HI | 144° C. |
| 168a | 3-methyl- | H | CH₃ | H | 4-tert.-butylbenzyl | HCl | 142° C. |

TABLE 1-continued

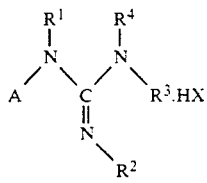

| Comp. No. | A | R¹ | R² | R³ | R⁴ | HX | mp./IR (film)[cm⁻¹] |
|---|---|---|---|---|---|---|---|
| 169a | 3-methyl-cyclohexyl | H | CH₃ | H | 4-tert.-butylbenzyl | CH₃COOH | 102° C. |
| 170a | 3-methyl-cyclohexyl | H | CH₃ | H | 4-tert.-butylbenzyl | C₂H₂O₄ | 173° C. |
| 171a | 3-methyl-cyclohexyl | H | H | H | 6,10-dimethylundec-2-yl | CH₃COOH | 3179, 3092, 2951, 2927, 2867, 1644, 1557, 1460 |
| 172a | 2,6-dimethyl-cyclohexyl | H | H | H | 3-(4-tert.-butylphenyl)-2-methylpropyl | HI | 3188, 2960, 2929, 2871, 1569, 1463 |
| 173a | 4-hyrdroxy cyclohexyl | H | H | H | 4-tert.-butylbenzyl | HI | 100° C. |
| 174a | 3-methyl-cyclohexyl | H | H | H | 4-tert.-butylbenzyl | HCl | 130° C. |
| 175a | 3-methyl-cyclohexyl | H | H | H | 4-tert.-butylbenzyl | CH₃COOH | 105° C. |
| 176a | 3-methyl-cyclohexyl | H | H | H | 4-tert.-butylbenzyl | C₂H₂O₄ | 95° C. |
| 177a | 3,3-dimethyl-cyclohexyl | H | H | H | 3-(4-tert.-butylphenyl)-2-methylpropyl | HCl | 100° C. |
| 178a | 3,3-dimethyl-cyclohexyl | H | H | H | 3-(4-tert.-butylphenyl)-2-methylpropyl | CH₃COOH | 100° C. |
| 179a | 3,3-dimethyl-cyclohexyl | H | H | H | 3-(4-tert.-butylphenyl)-2-methylpropyl | C₂H₂O₄ | 112° C. |
| 180a | cyclopentyl | H | H | H | 4-tert.-butylbenzyl | HI | 88° C. |
| 181a | cyclopentyl | H | H | H | 3-(4-tert.-butylbenzyl)-2-methylpropyl | CH₃COOH | 3304, 3184, 3089, 2962, 2871, 1650, 1561, 1401 |
| 182a | cyclopentyl | H | H | H | 6,10-dimethylundec-2-yl | CH₃COOH | 3175, 2955, 2927, 2869, 1646, 1560, 1400 |
| 183a | cycloheptyl | H | H | H | 4-tert.-butylbenzyl | HI | 3253, 3180, 2960, 2927, 2857, 1645, 1626, 1460 |
| 184a | cyclooctyl | H | H | H | 4-tert.-butylbenzyl | HI | 90° C. |
| 185a | cyclooctyl | H | H | H | 3-(4-tert.-butylphenyl)-2-methylpropyl | CH₃COOH | 3186, 3091, 2961, 2924, 2868, 1649, 1561, 1404 |
| 186a | cyclooctyl | H | H | H | 6,10-dimethyl-undec-2-yl | CH₃COOH | 2951, 2925, 2867, 1643, 1559, 1465, 1400 |
| 187a | cyclohexyl | H | isopropyl | H | 4-tert.-butylbenzyl | CH₃COOH | 72° C. |
| 188a | cyclohexyl | H | but-2-yl | H | 4-tert.-butylbenzyl | CH₃COOH | 80° C. |
| 1b | p-tert.-butyl-benzyl | H | CH₃ | H | 3-(4-tert.-butylphenyl)-2-methylpropyl | HCl | 125° C. |
| 2b | p-tert.-butyl-benzyl | H | CH₃ | R³ + R⁴ = 4-tert.-butyl-piperidinyl | | HI | 155° C. |
| 3b | p-tert.-butyl-benzyl | H | CH₃ | H | 4-tert.-butylbenzyl | — | 2963, 2904, 2867, 1863, 1637, 1513, 1476, 1464 |
| 4b | p-tert.-butyl-benzyl | H | CH₃ | H | 4-tert.-butylbenzyl | HCl | 125° C. |
| 5b | p-tert.-butyl-benzyl | H | CH₃ | H | 4-tert.-butylbenzyl | CH₃COOH | 2963, 2905, 1638, 1568, 1514, 1477, 1393, 1365 |
| 6b | p-tert.-butyl-benzyl | H | CH₃ | H | cyclohexylmethyl | HI | 186° C. |
| 7b | p-tert.-butyl-benzyl | H | CH₃ | H | 3,5,5-trimethylhexyl | HI | 165° C. |
| 8b | benzyl | H | n-butyl | H | 3-(4-tert.-butylphenyl)-2-methylpropyl | CH₃COOH | 2958, 2928, 2869, 1639, 1510, 1495, 1453, 1362 |
| 9b | p-tert.-butyl-benzyl | H | n-butyl | R³ + R⁴ = cis-2,6-dimethyl-morpholin-4-yl | | CH₃COOH | 2963, 2935, 2872, 1627, 1590, 1269, 1087 |
| 10b | p-tert.-butyl-benzyl | H | n-butyl | R³ + R⁴ = cis-2,6-dimethyl-morpholin-4-yl | | HCl | 60° C. |
| 11b | p-tert.-butyl-benzyl | H | n-butyl | H | 2,2-dimethylpropyl | HCl | 88° C. |
| 12b | p-tert.-butyl-benzyl | H | n-butyl | H | 2,2-dimethylpropyl | CH₃COOH | 2962, 2872, 1630, 1574, 1394, 1366 |
| 13b | p-tert.-butyl-benzyl | H | n-butyl | H | 4-tert.-butylbenzyl | CH₃COOH | 2962, 2906, 1634, 1570, 1394 |
| 14b | p-tert.-butyl-benzyl | H | n-butyl | H | 4-tert.-butylbenzyl | HCl | 102° C. |
| 15b | p-tert.-butyl-benzyl | H | n-butyl | H | 3-(4-tert.-butylphenyl)-2-methylpropyl | HCl | 95 to 100° C. |
| 16b | p-tert.-butyl-benzyl | H | n-butyl | H | 3-(4-tert.-butylphenyl)-2-methylpropyl | CH₃COOH | 2962, 2933, 1633, 1571, 1394, 1364 |
| 17b | p-tert.-butyl-benzyl | H | n-butyl | H | n-pentyl | — | |

TABLE 1-continued

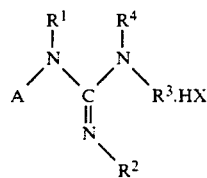

| Comp. No. | A | R¹ | R² | R³ | R⁴ | HX | mp./IR (film)[cm⁻¹] |
|---|---|---|---|---|---|---|---|
| 18b | p-tert.-butyl-benzyl | H | H | H | n-hexyl | HI | 156° C. |
| 19b | p-tert.-butyl-benzyl | H | H | H | n-heptyl | HI | 135° C. |
| 20b | p-tert.-butyl-benzyl | H | H | H | n-octyl | HI | 113° C. |
| 21b | p-tert.-butyl-benzyl | H | H | H | n-nonyl | HI | 3247, 3179, 2956, 2924, 2854, 1649, 1629, 1465 |
| 22b | p-tert.-butyl-benzyl | H | H | H | n-decyl | HI | 3248, 3179, 2957, 2925, 2855, 1649, 1630, 1466 |
| 23b | p-tert.-butyl-benzyl | H | H | H | n-dodecyl | HI | 3247, 3180, 2957, 2924, 2854, 1649, 1630, 1466 |
| 24b | p-tert.-butyl-benzyl | H | CH₃ | H | n-hexyl | HI | 177° C. |
| 25b | p-tert.-butyl-benzyl | H | CH₃ | H | n-octyl | HI | 122° C. |
| 26b | p-tert.-butyl-benzyl | H | CH₃ | H | n-decyl | HI | 85° C. |
| 27b | p-tert.-butyl-benzyl | H | CH₃ | H | n-dodecyl | HI | 96° C. |
| 28b | p-tert.-butyl-benzyl | H | CH₃ | H | 2,2-dimethylpropyl | HI | 165° C. |
| 29b | p-tert.-butyl-benzyl | H | CH₃ | H | 3-methyl-butyl | HI | 137° C. |
| 30b | p-tert.-butyl-benzyl | H | CH₃ | R³ + R⁴ = piperidinyl | | HI | 82° C. |
| 31b | p-tert.-butyl-benzyl | H | CH₃ | H | phenethyl | HI | 87° C. |
| 32b | p-tert.-butyl-benzyl | H | CH₃ | H | benzyl | HI | 124° C. |
| 33b | p-tert.-butyl-benzyl | H | CH₃ | H | 3-(4-tert.-butylphenyl)-2-methylpropyl | HI | 165° C. |
| 34b | p-tert.-butyl-benzyl | H | CH₃ | H | 2-ethyl-hexyl | HI | 65° C. |
| 35b | p-tert.-butyl-benzyl | H | CH₃ | H | n-tridecyl | HI | 105° C. |
| 36b | p-tert.-butyl-benzyl | H | CH₃ | H | 4-methoxy-phenethyl | HI | 137° C. |
| 37b | p-tert.-butyl-benzyl | H | CH₃ | H | 6-ethyl-4-oxa-decyl | HI | 3218, 2959, 2929, 2870, 1623, 1462, 1380, 1109 |
| 38b | p-tert.-butyl-benzyl | H | CH₃ | H | 4-phenyl-but-2-yl | HI | 102° C. |
| 39b | p-tert.-butoxy-benzyl | H | H | H | 4-tert.-butyl-cyclohexylmethyl | HI | 192° C. |
| 40b | p-tert.-butyl-benzyl | H | H | H | 4-tert.-butyl-cyclohexylmethyl | HI | 192° C. |
| 41b | p-tert.-butyl-benzyl | H | H | H | 1-phenyl-ethyl | HI | 70° C. |
| 42b | p-tert.-butyl-benzyl | H | H | H | 4-phenyl-but-2-yl | HI | 75° C. |
| 43b | p-tert.-butyl-benzyl | H | H | H | 3-diethylaminopropyl | HI | 3243, 3179, 2964, 2870, 2822, 1629, 1465, 1366 |
| 44b | p-tert.-butyl-benzyl | H | H | H | 4-methoxy-phenethyl | HI | 3303, 3185, 3164, 1643, 1632, 1595, 1512, 1242 |
| 45b | p-tert.-butyl-benzyl | H | H | H | phenethyl | HI | 130° C. |
| 46b | p-tert.-butyl-benzyl | H | H | H | 2-ethylhexyl | HI | 3251, 3181, 2960, 2929, 2872, 1649, 1630, 1464 |
| 47b | p-tert.-butyl-benzyl | H | H | H | benzyl | HI | 58° C. |
| 48b | p-tert.-butyl-benzyl | H | H | R³ + R⁴ = 4-tert.-butyl-piperidinyl | | HI | 183° C. |
| 49b | p-tert.-butyl-benzyl | H | H | H | 4-tert.-butylbenzyl | HI | 182° C. |
| 50b | p-tert.-butyl-benzyl | H | H | H | 3-(4-tert.-butylphenyl)-2-methylpropyl | HI | 152° C. |
| 51b | p-tert.-butyl-benzyl | H | H | H | tridecyl | HI | 89° C. |
| 52b | p-tert.-butyl-benzyl | H | H | H | 6-ethyl-4-oxa-decyl | HI | 100° C. |

TABLE 1-continued

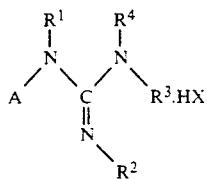

| Comp. No. | A | R¹ | R² | R³ | R⁴ | HX | mp./IR (film)[cm⁻¹] |
|---|---|---|---|---|---|---|---|
| 53b | p-tert.-butyl-benzyl | H | H | R³ + R⁴ =piperidinyl | | HI | 72° C. |
| 54b | p-tert.-butyl-benzyl | H | $CH_3$ | H | 4-tert.-butyl-cyclohexylmethyl | HI | 125° C. |
| 55b | p-tert.-butyl-benzyl | H | $CH_3$ | H | 3-diethylaminpropyl | HI | 3210, 3102, 2964, 2870, 1620, 1458, 1383, 1364 |
| 56b | p-tert.-butyl-benzyl | H | $CH_3$ | H | 1-phenyl-ethyl | HI | 163° C. |
| 57b | p-(1,1-dimethyl-ethyl)-benzyl | H | H | H | n-hexyl | — | |
| 58b | p-(1,1-dimethyl-ethyl)-benzyl | H | H | H | n-heptyl | — | |
| 59b | p-(1,1-dimethyl-ethyl)-benzyl | H | H | H | n-octyl | — | |
| 60b | p-(1,1-dimethyl-ethyl)-benzyl | H | H | H | n-nonyl | — | |
| 61b | p-(1,1-dimethyl-ethyl)-benzyl | H | H | H | tert.-butylbenzyl | — | |
| 62b | p-(1,1-dimethyl-ethyl)-benzyl | H | H | H | 3-methylbutyl | — | |
| 63b | p-(1,1-dimethyl-ethyl)-benzyl | H | H | H | 3-(4-tert.-butylphenyl)-2-methylpropyl | — | |
| 64b | p-tert.-butoxy-benzyl | H | H | H | n-hexyl | — | |
| 65b | p-tert.-butoxy-benzyl | H | H | H | n-heptyl | — | |
| 66b | p-tert.-butoxy-benzyl | H | H | H | n-octyl | — | |
| 67b | p-tert.-butoxy-benzyl | H | H | H | n-nonyl | — | |
| 68b | p-tert.-butoxy-benzyl | H | H | H | n-decyl | — | |
| 69b | p-tert.-butoxy-benzyl | H | H | H | 3-methylbutyl | — | |
| 70b | p-tert.-butoxy-benzyl | H | H | H | tert.-butylbenzyl | — | |
| 71b | p-tert.-butoxy-benzyl | H | H | H | tert.-buoxybenzyl | — | |
| 72b | p-tert.-butoxy-benzyl | H | H | H | n-octyl | — | |
| 73b | p-(1,1,2-trimethylpropyl)-benzyl | H | H | H | n-hexyl | — | |
| 74b | p-(1,1,2-trimethylpropyl)-benzyl | H | H | H | n-heptyl | — | |
| 75b | p-(1,1,2-trimethylpropyl)-benzyl | H | H | H | n-octyl | — | |
| 76b | p-(1,1,2-trimethylpropyl)-benzyl | H | H | H | n-nonyl | — | |
| 77b | p-(1,1,2-trimethylpropyl)-benzyl | H | H | H | n-decyl | — | |
| 78b | p-tert.-butyl-benzyl | H | $CH_3$ | H | cyclohexylmethyl | HCl | 155° C. |
| 79b | p-tert.-butyl-benzyl | H | $CH_3$ | H | cyclohexylmethyl | $CH_3COOH$ | 82° C. |
| 80b | p-tert.-butyl-benzyl | H | $CH_3$ | H | cyclohexylmethyl | $(COOH)_2$ | ½° C. |
| 81b | p-tert.-butyl-benzyl | H | $CH_3$ | H | 3,5,5-trimethylhexyl | $(COOH)_2$ | 180° C. |
| 82b | p-tert.-butyl-benzyl | H | $CH_3$ | H | 3,5,5-trimethylhexyl | $CH_3COOH$ | 75° C. |
| 83b | p-tert.-butyl-benzyl | H | $CH_3$ | H | 3,5,5-trimethylhexyl | HCl | 107° C. |
| 84b | p-tert.-butyl-benzyl | H | $CH_3$ | H | n-hexyl | HCl | 105° C. |

TABLE 1-continued

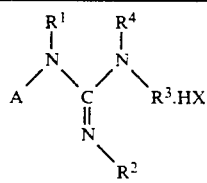

| Comp. No. | A | R$^1$ | R$^2$ | R$^3$ | R$^4$ | HX | mp./IR (film)[cm$^{-1}$] |
|---|---|---|---|---|---|---|---|
| 85b | p-tert.-butyl-benzyl | H | CH$_3$ | H | n-hexyl | CH$_3$COOH | 110° C. |
| 86b | p-tert.-butyl-benzyl | H | CH$_3$ | H | n-hexyl | (COOH)$_2$ | 185° C. |
| 87b | p-tert.-butyl-benzyl | H | CH$_3$ | H | 3-methylbutyl | (COOH)$_2$ | 182° C. |
| 88b | p-tert.-butyl-benzyl | H | H | H | 3-methylbutyl | CH$_3$COOH | 72° C. |
| 89b | p-tert.-butyl-benzyl | H | H | H | 3-methylbutyl | HCl | 105° C. |
| 90b | p-tert.-butyl-benzyl | H | H | H | 6-ethyl-4-oxa-decyl | HCl | oil, 3260, 3173, 2959, 2930, 2871, 1655, 1637, 1464 |
| 91b | p-tert.-butyl-benzyl | H | H | H | 6-ethyl-4-oxa-decyl | CH$_3$COOH | oil, 2959, 2929, 2870, 1653, 1560, 1515, 1403, 1110 |
| 92b | p-tert.-butyl-benzyl | H | H | H | 6-ethyl-4-oxa-decyl | (COOH)$_2$ | oil, 3183, 2958, 2929, 2870, 1633, 1462, 1220, 1109 |
| 93b | p-tert.-butyl-benzyl | H | H | H | 4-tert.-butoxybenzyl | (COOH)$_2$ | 118° C. |
| 94b | p-tert.-butyl-benzyl | H | H | H | 4-tert.-butoxybenzyl | CH$_3$COOH | 168° C. |
| 95b | p-tert.-butyl-benzyl | H | CH$_3$ | H | 3-(tert.-butylphenyl)-2-methylpropyl | CH$_3$COOH | 97° C. |
| 96b | p-tert.-butyl-benzyl | H | CH$_3$ | H | 3-(4-tert.-butylphenyl)-2-methylpropyl | H$_3$BO$_3$ | 149° C. |
| 97b | p-tert.-butyl-benzyl | H | CH$_3$ | H | 3-(4-tert.-butylphenyl)-2-methylpropyl | — | 2960, 2903, 2867, 1636, 1512, 1474, 1462, 1362 |
| 98b | p-tert.-butyl-benzyl | H | H | H | 2-ethylhexyl | HCl | 80° C. |
| 99b | p-tert.-butyl-benzyl | H | H | H | 2-ethylhexyl | CH$_3$COOH | 2959, 2928, 2870, 1569, 1462, 1402, 1363, 1269 |
| 100b | p-tert.-butyl-benzyl | H | H | R$^3$ + R$^4$ = | 4-tert.-butyl-piperidinyl | HCl | 250° C. |
| 101b | p-tert.-butyl-benzyl | H | H | R$^3$ + R$^4$ = | 4-tert.-butyl-piperidinyl | CH$_3$COOH | |
| 102b | p-tert.-butyl-benzyl | H | H | H | 3-(4-tert.-butylphenyl)-2-methylpropyl | HCl | 90° C. |
| 103b | p-tert.-butyl-benzyl | H | H | H | 3-(4-tert.-butylphenyl)-2-methylpropyl | CH$_3$COOH | 3278, 3198, 2961, 1635, 1606, 1561, 1516, 1409 |
| 104b | p-tert.-butyl-benzyl | H | H | H | 4-hydroxybenzyl | HCl | 3323, 3263, 3170, 2961, 1651, 1614, 1513, 1267 |
| 105b | p-tert.-butyl-benzyl | H | H | H | 4-hydroxybenzyl | CH$_3$COOH | 3180, 3026, 2962, 1645, 1614, 1554, 1462, 1409 |
| 106b | p-tert.-butyl-benzyl | H | H | CH$_3$ | 2,5,7,7-tetramethyl-octyl | HI | 58° C. |
| 107b | p-tert.-butyl-benzyl | H | CH$_3$ | H | 4-tert.-butylbenzyl | HI | 90° C. |
| 108b | p-tert.-butyl-benzyl | H | H | R$^3$ + R$^4$ = | 3-(1,5-dimethylhexyl)-pyrrolidinyl | HJ | 172° C. |
| 109b | p-tert.-butyl-benzyl | H | H | R$^3$ + R$^4$ = | 3-(1,5-dimethylhexyl)-pyrrolidinyl | HCl | 190° C. |
| 110b | p-tert.-butyl-benzyl | H | H | R$^3$ + R$^4$ = | 3-(1,5-dimethylhexyl)-pyrrolidinyl | CH$_3$COOH | 2955, 2928, 2868, 1610, 1573, 1465, 1448, 1402 |
| 111b | p-tert.-butyl-benzyl | H | H | H | n-undecyl | HI | 3249, 3181, 2956, 2924, 2853, 1649, 1629, 1464 |
| 112b | p-tert.-butyl-benzyl | H | H | H | 6-hydroxyhexyl | HI | 3287, 3198, 2932, 2859, 1650, 1629, 1547, 1462 |
| 113b | p-tert.-butyl-benzyl | H | H | H | 2-(2-hydroxyethoxy)-ethyl | HI | 3299, 3188, 2958, 2869, 1651, 1631, 1122, 1065 |
| 114b | p-tert.-butyl-benzyl | H | H | H | 6-hydroxy-6-methyl-hept-2-yl | HI | 3297, 3188, 2964, 2867, 1626, 1602, 1556, 1462 |
| 115b | p-tert.-butyl-benzyl | H | H | H | 6,10-dimethyl-undec-2-yl | HI | 3249, 3180, 2954, 2926, 2867, 1646, 1626, 1462 |
| 116b | p-tert.-butyl-benzyl | H | H | H | 2,2-dimethylpropyl | HI | 85° C. |
| 117b | p-tert.-butyl-benzyl | H | H | H | 3-methylbutyl | HI | 122° C. |
| 118b | p-tert.-butyl-benzyl | H | CH$_3$ | H | n-butyl | HI | 135° C. |
| 119b | p-tert.-butyl-benzyl | H | CH$_3$ | H | n-pentyl | HI | 147° C. |

TABLE 1-continued

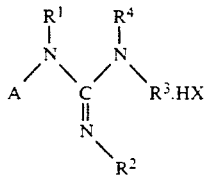

| Comp. No. | A | R¹ | R² | R³ | R⁴ | HX | mp./IR (film)[cm⁻¹] |
|---|---|---|---|---|---|---|---|
| 120b | p-tert.-butyl-benzyl | H | n-butyl | H | cis-2,6-dimethyl-morpholin-4-yl | — | 2962, 2931, 2904, 2869, 1637, 1375, 1144, 1086 |
| 121b | p-tert.-butyl-benzyl | H | n-butyl | H | 2,2-dimethylpropyl | — | 2956, 2904, 2867, 1649, 1513, 1476, 1464, 1362 |
| 122b | p-tert.-butyl-benzyl | H | n-butyl | H | 4-tert.-butylbenzyl | — | 2959, 2931, 2904, 2868, 1633, 1513, 1463, 1362 |
| 123b | p-tert.-butyl-benzyl | H | n-butyl | H | 3-(4-tert.-butylphenyl)-2-methylpropyl | — | 2960, 2928, 2869, 1640, 1512, 1462, 1362, 1269 |
| 124b | p-tert.-butyl-benzyl | H | H | H | n-butyl | HI | 3248, 3182, 2959, 2932, 2870, 1649, 1630, 1463 |
| 125b | p-tert.-butyl-benzyl | H | H | H | n-pentyl | HI | 120° C. |

Use examples

The active ingredients N-1-(4-tert-butylphenyl)-N-3-allylguanidine (A), N-1-(4-tert-butylphenyl)-N-2-cyclohexyl-n-3-N,N-dimethylamino-n-propyl)guanidine (B) and N-1-(4-tert-butylphenyl)-N-2-DE-A 31 08 564 were used for comparison purposes.

Example 1

Action on Pyrenophora teres

Barley seedlings of the "Igri" variety were sprayed to runoff at the two-leaf stage with aqueous suspensions consisting (dry basis) of 80% of active ingredient and 20% of emulsifier. After 24 hours the plants were inoculated with a spore suspension of the fungus *Pyrenophara teres*, and set up for 48 hours in a high-humidity climatic cabinet at 18° C. The plants were then cultivated for a further 5 days in the greenhouse at 20 to 22° and a relative humidity of 70° C. The extend of fungus spread was then assessed.

The results show that active ingredients, 1a, 5a, 7a, 11a, 13a, 27a, 28a, 31a, 32a, 39a, 49a, 54a, 57a, 75a, 1b, 3b, 4b, 7b, 8b, 13b, 14b, 15b, 16b, 18b, 20b, 22b, 23b, 25b, 26b, 34b, 37b, 52b, and 54b, applied as 0.05wt% spray liquors, have a better fungicidal action (85%) than prior art comparative ingredients A, B and C (55%).

Example 2

Action on wheat mildew

Leaves of pot-grown wheat seedlings of the "Kanzler" variety were sprayed with 0.025% aqueous spray liquors containing (dry basis) 80% of active ingredient and 20% of emulsifier, and dusted, 24 hours after the sprayed-on liquor had dried, with spores of wheat mildew (Erysiphe graminis var. tritici). The plants were then set up in the greenhouse at from 20 to 22° C. and a relative humidity of 75 to 80%. The extent of fungus spread was assessed after 7 days.

The results show that active ingredients 1a, 15a, 26a, 32a, 47a, 49a, 56a, 69a, 70a, 2b, 6b, 9b, 11b, 12b, 13b, 29b, 31b, 34b, 35b, 36b, 38b, 45b and 46b, applied as 0.025wt% spray liquors, have a better fungicidal action (85%) than prior art comparative ingredients B and C (60%0.

We claim:

1. A substituted guanidine of formula I

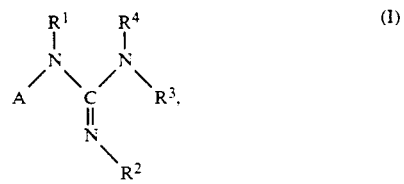

where:
is cycloalky which has 5 to 12 carbon atoms in the ring and may carry up to three of the following substituents: hydroxyl, halogen, $C_1$-$C_{10}$-alkyl, $C_1$-$C_{10}$-alkoxy, $C_1$-$C_{10}$-haloalkyl and $C_1$-$C_8$-alkoxy-$C_1$-$C_8$-alkyl;
$R^1$, $R^2$ and $R^3$ are each hydrogen or $C_1$-$C_4$-alkyl, and
$R^4$ is $C_5$-$C_{18}$-alkyl which may be interrupted by oxygen, or is a $C_5$-$C_{18}$-alkenyl group, a $C_4$-$C_{18}$-alkynyl group or phenyl-$C_1$-$C_6$-alkyl group, where these groups may carry up to three of the following substituents: hydroxyl, halogen, cyano, $C_1$-$C_7$-alkoxy or up to two amino, $C_1$-$C_4$-alkylamino or di-$C_1$-$C_4$-alkylamino substituents, and the phenyl moiety of the phenylalkyl group may additionally carry a phenoxy group or up to three $C_2$-$C_4$-alkenyl groups, $C_1$-$C_4$-alkoxy-$C_1$-$C_4$alkyl groups or $C_1$-$C_6$-alkyl groups which may be unsubstituted or partially or completely halogenated, or $C_5$-$C_6$-cycloalkyl-$C_1$-$C_8$-alkyl where the cycloalkyl ring may carry up to three $C_1$-$C_4$-alkyl groups or up to two hydroxyl or trifluoromethyl groups; or the plant tolerated mineral acid slats or metal complexes thereof.

2. A guanidine as set forth in claim 1, where the substituents have the following meanings:
is cycloalkyl which has 5 to 12 carbon atoms in the ring and may carry up to three of the following substituents: hydroxyl, fluoro, chloro, $C_1$-$C_8$-alkyl, $C_1$-$C_8$-alkoxy, $C_1$-$C_4$-haloalkyl and $C_1$-$C_6$-alkoxy-$C_1$-$C_5$-alkyl;
$R^1$, $R^2$ and $R^3$ are each hydrogen or $C_1$-$C_4$alkyl;
$R^4$ is $C_5$-$C_{18}$-alkyl which may be interrupted by oxygen, or is $C_5$-$C_{18}$-alkenyl, $C_4$-$C_{18}$-alkynyl or phenyl-$C_1$-$C_6$-alkyl, where these groups may carry up to three of the following substituents: hydroxyl, chloro, bromo, cyano or $C_1$-$C_7$-alkoxy, or up to two amino, $C_1$-$C_4$-alkylamino or di-($C_1$-$C_4$-)-alkylamino substituents, and the phenyl moiety of the phenylalkyl group may additionally carry a phenoxy group or up to three $C_2$-$C_4$-alkenyl groups, $C_1$-$C_4$-alkoxy-$C_1$-$C_4$-alkyl groups or $C_1$-$C_4$-alkyl groups which may be unsubstituted or partially or completely halogenated; or $C_5$-$C_6$-cycloalkyl-$C_1$-$C_4$-alkyl groups or up to two trifluoromethy groups;

or the plant-tolerted mineral acid salts or metal complexes thereof.

3. A fungicidal composition comprising a fungicidally effective amount of at least one substituted guanidine of the formula I, as set forth in claim 1, or a plant-tolerated mineral acid salt or metal complex thereof and a liquid or solid carrier.

4. A process for combating fungi, wherein a fungicidally effective amount of a substituted guanidine of the Formula I, as set forth in claim 1, or a plant-tolerated mineral acid salt or metal complex thereof, is applied to fungi, or to plants or their habitat threatened by fungus attack, or on the seeds of the threatened plants.

5. A substituted guanidine as set forth in claim 1, wherein A is cyclohexyl; $R^1$, $R^2$ and $R^3$ are each hydrogen; and $R^4$ is 4-tertiarybutylbenzyl.

6. A substituted guanidine of formula I:

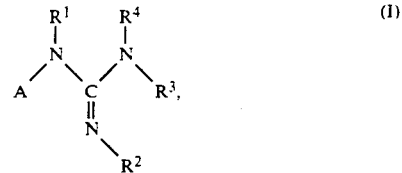

where:

is cycloalkyl which has 5 to 12 carbon atoms in the ring and may carry up to three of the following substituents: halogen, $C_1$-$C_{10}$-alkyl, $C_1$-$C_{10}$-alkoxy, and $C_1$-$C_{10}$-haloalkyl;

$R^1$, $R^2$ and $R^3$ are each hydrogen or $C_1$-$C_4$-alkyl; and $R^4$ is 4-tertiarybutylphenyl, $C_1$-$C_4$-alkyl or is $C_5$-$C_{18}$-alkyl which may carry up to three of the following substituents: halogen or $C_1$-$C_7$-alkoxy or up to two amino groups or the plant-tolerated salts or metal complexes thereof.

* * * * *

UNITED STATES PATENT AND TRADEMARK OFFICE
CERTIFICATE OF CORRECTION

PATENT NO. : 5,126,374

DATED : June 30, 1992

INVENTOR(S) : Matthias ZIPPLIES et al.

It is certified that error appears in the above—identified patent and that said Letters Patent is hereby corrected as shown below:

In the Abstract, fourth line from the bottom, "I.HX" should read -- I·HX --

Claim 1, Column 34, line 36, "is cycloalky" should read -- A is cycloalkyl --

Claim 1, Column 34, line 51, insert "-" between "$C_4$" and "alkyl"

Claim 1, Column 34, line 57, "slats" should read -- salts --

Claim 2, column 34, line 61, insert -- A -- before "is cycloalkyl"

Claim 2, column 34, line 66, insert "-" between "$C_4$" and "alkyl"

Claim 6, column 36, line 15, insert -- A -- before "is"

Signed and Sealed this

Twelfth Day of October, 1993

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,126,374
DATED : June 30, 1992
INVENTOR(S) : ZIPPLIES et al.

It is certified that error appears in the above-identified patent and that said Letters Patent is hereby corrected as shown below:

Claim 2, column 35, line 8, "$C_4$" should read --$C_6$--.

Claim 2, column 35, line 11, after "alkyl" insert
 --where the cycloalkyl ring may carry up to three $C_1$-$C_4$-alkyl--.

Signed and Sealed this

Fourteenth Day of June, 1994

*Attest:*

BRUCE LEHMAN

*Attesting Officer*   *Commissioner of Patents and Trademarks*